(12) United States Patent
Burckhardt et al.

(10) Patent No.: US 8,430,989 B2
(45) Date of Patent: Apr. 30, 2013

(54) HYDROXYALDIMINE-CONTAINING POLYURETHANE COMPOSITION

(75) Inventors: Urs Burckhardt, Zurich (CH); Ursula Stadelmann, Zurich (CH)

(73) Assignee: Sika Technology AG, Baar (CH)

( * ) Notice: Subject to any disclaimer, the term of this patent is extended or adjusted under 35 U.S.C. 154(b) by 0 days.

(21) Appl. No.: 13/108,280

(22) Filed: May 16, 2011

(65) Prior Publication Data

US 2011/0214810 A1    Sep. 8, 2011

Related U.S. Application Data

(63) Continuation of application No. PCT/EP2009/066183, filed on Dec. 2, 2009.

(30) Foreign Application Priority Data

Dec. 2, 2008    (EP) .................................... 08170474

(51) Int. Cl.
| | |
|---|---|
| *C04B 37/00* | (2006.01) |
| *C09J 4/00* | (2006.01) |
| *C09J 101/00* | (2006.01) |
| *C09J 201/00* | (2006.01) |
| *C08G 18/00* | (2006.01) |
| *C07C 257/00* | (2006.01) |

(52) U.S. Cl.
USPC ......... 156/325; 156/330.9; 525/452; 564/248

(58) Field of Classification Search ............... 156/330.9, 156/325; 525/452; 564/248
See application file for complete search history.

(56) References Cited

U.S. PATENT DOCUMENTS

| | | | |
|---|---|---|---|
| 3,743,667 A | 7/1973 | Wagner et al. | |
| 3,770,799 A | 11/1973 | Wagner et al. | |
| 3,835,191 A | 9/1974 | Wagner et al. | |
| 5,955,199 A * | 9/1999 | Johnson et al. | 428/423.1 |
| 2008/0199621 A1* | 8/2008 | Burckhardt et al. | 427/393.5 |
| 2009/0176944 A1 | 7/2009 | Burckhardt | |

FOREIGN PATENT DOCUMENTS

| | | |
|---|---|---|
| DE | 18 14 832 A1 | 7/1970 |
| EP | 1 975 190 A1 | 10/2008 |
| WO | WO 2007/036571 A1 | 4/2007 |

OTHER PUBLICATIONS

Houben-Weyl, Edited by Eugen Müller et al., "Methoden Der Organischen Chemie [Methods of Organic Chemistry]", 1958, vol. XI/2, pp. 73-99 (with English language translation).

Notification of Transmittal of Translation of the International Preliminary Report on Patentability (Forms PCT/IB/338 and PCT/IB/373) and the Written Opinion of the International Searching Authority ( Form PCT/ISA/237) issued on Jun. 16, 2011, in the corresponding International Application No. PCT/EP2009/066183.

International Search Report (PCT/ISA/210) issued on Feb. 25, 2010, by European Patent Office as the International Searching Authority for International Application No. PCT/EP2009/066183.

Written Opinion (PCT/ISA/237) issued on Feb. 25, 2010, by European Patent Office as the International Searching Authority for International Application No. PCT/EP2009/066183.

* cited by examiner

*Primary Examiner* — Michael Orlando

(74) *Attorney, Agent, or Firm* — Buchanan Ingersoll & Rooney PC

(57) ABSTRACT

A composition that includes aldimines of Formula (I). The composition can be a two-component polyurethane composition. The composition can have a long open time, but build up an early strength quickly, and in the cured state can have high tensile strength and a high modulus of elasticity. The composition can be odorless or at least low-odor before, during and after curing.

23 Claims, No Drawings

HYDROXYALDIMINE-CONTAINING POLYURETHANE COMPOSITION

RELATED APPLICATIONS

This application claims priority as a continuation application under 35 U.S.C. §120 to PCT/EP2009/066183, which was filed as an International Application on Dec. 2, 2009 designating the U.S., and which claims priority to European Application No. 08170474.4 filed in Europe on Dec. 2, 2008. The entire contents of these applications are hereby incorporated by reference in their entireties.

FIELD

Polyurethane compositions are disclosed as well as their use, for example, as a two-component adhesive, sealant, filling compound, coating or floor covering.

BACKGROUND INFORMATION

Polyurethane compositions that have isocyanate groups have been used in a wide variety of applications, for example, as adhesive, sealant, filling compound, coating or floor covering. While one-component polyurethane compositions can be used as such and cure after their application by contact with moisture and/or by means of heat, two-component polyurethane compositions include two components that are stored separately from one another—in general one component with free isocyanate groups and one component with free hydroxyl groups—which are thoroughly mixed for use of the composition just shortly before or during their application and thereupon cure. For two-component polyurethane compositions, it can be desirable that the compositions cure as quickly as possible in a sufficiently long pot life and processing time, for example, to build up strength as quickly as possible after application and thus to be available to be subject to load or working after a short time, thus can be moved with parts joined by adhesive or can be removed by attaching holding devices, or thus an applied coating can be walked on, recoated, or polished.

In a two-component polyurethane composition, the curing can be accelerated, for example, by supplying heat or by using strong or high-dose catalysts. The supply of heat can bring about an elevated cost of administration, can damage the substrates, and can result in the formation of bubbles and loss of adhesion, and the use of strong or high-dose catalysts can cause losses in the shelf life and the long-term stability of the composition, and can result, for example, in a shortening of the open time of the composition.

Two-component polyurethane compositions, whose hydroxyl-group-containing components in addition have free primary or secondary amino groups of jointly contained polyamines, can cure especially quickly, in this case have very little tendency to form bubbles and exhibit very good mechanical properties, since more urea groups are produced, which generally increase the strength and elasticity of polyurethanes. The reactivity of free amino groups relative to isocyanate groups can be high, however, in such a way that such compositions can have too short a pot life and processing time (open time) for most applications. In addition, amines in the air often tend to form crusts by reaction with $CO_2$ ("blushing") and/or can have disadvantages because of their toxicity relative to the operational safety and ecology.

Instead of free amines, so-called blocked amines with hydrolytically activatable amino groups can be used, for example in the form of imines or oxazolidines. The latter do not have any blushing and make possible two-component compositions with somewhat longer open times. The use of blocked amines in polyurethane compositions can result in other difficulties, for example, caused by the fact that the substances used for blocking the amino groups—typically aldehydes or ketones—can be released during the curing of the composition. In most cases, the latter are volatile and strong-smelling and can result in, for example, strong odors and irritation.

Two-component polyurethane compositions that contain aldimines with additional reactive groups, which cure quickly and odor-free, are known from WO 2007/036571 A1. During curing, these aldimines release a relatively low-volatile aldehyde, which remains in the cured composition and exerts a more or less pronounced softening action on the latter. As a result, these compositions remain limited with respect to their mechanical properties, for example, the achievable values for the modulus of elasticity, and therefore do not remain accessible to all applications.

SUMMARY

A composition is disclosed, comprising:

a) at least one aldimine A of Formula (I),

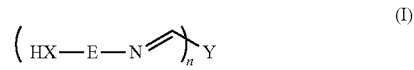

wherein n stands for 2 or 3 or 4,

E either represents a divalent hydrocarbon radical with 3 to 20 C atoms, or together with $R^{11}$ for a trivalent hydrocarbon radical with 3 to 20 C atoms, wherein E optionally contains heteroatoms in the form of ether-oxygen or tertiary amine-nitrogen, Y represents an n-value organic radical with 6 to 30 C atoms, which optionally contains nitrogen and/or oxygen atoms in the form of tertiary amino groups, or ether, ester, carbonate, amide, urethane or urea groups, X represents O or S or N—$R^{10}$ or N—$R^{11}$, wherein $R^{10}$ represents a monovalent hydrocarbon radical with 1 to 20 C atoms, which optionally contains at least one carboxylic acid ester, nitrile, nitro, phosphonic acid ester, sulfonic or sulfonic acid ester group, and $R^{11}$ together with E represents a trivalent hydrocarbon radical with 3 to 20 C atoms, which optionally contains heteroatoms in the form of ether-oxygen or tertiary amine-nitrogen; and b) at least one polyisocyanate P.

An aldimine of Formula (III) is disclosed

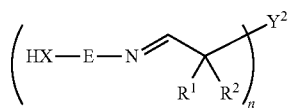

wherein
$R^1$ and $R^2$ either
independently of one another in each case represents a monovalent hydrocarbon radical with 1 to 12 C atoms,
or
together represent a divalent hydrocarbon radical with 4 to 12 C atoms, which is part of an optionally substituted, carbocyclic ring with 5 to 8 C atoms;
$Y^2$ represents an n-value organic radical with 1 to 24 C atoms, which optionally contains nitrogen and/or oxygen atoms in the form of tertiary amino groups, or ether, ester, carbonate, amide, urethane or urea groups;
E either represents a divalent hydrocarbon radical with 3 to 20 C atoms, or together with $R^{11}$ represents a trivalent hydrocarbon radical with 3 to 20 C atoms, wherein E optionally contains heteroatoms in the form of ether-oxygen or tertiary amine-nitrogen,
X represents O or S or $N-R^{10}$ or $N-R^{11}$,
wherein
$R^{10}$ represents a monovalent hydrocarbon radical with 1 to 20 C atoms, which optionally contains at least one carboxylic acid ester, nitrile, nitro, phosphonic acid ester, sulfonic or sulfonic acid ester group, and
$R^{11}$ together with E represents a trivalent hydrocarbon radical with 3 to 20 C atoms, which optionally contains heteroatoms in the form of ether-oxygen or tertiary amine-nitrogen;
and n represents 2 or 3 or 4.

A method for adhesive bonding a substrate S1 to a substrate S2 is disclosed, comprising:
i) applying a composition to a substrate S1; and
ii) bonding the applied composition to a substrate S2 within an open time of the composition;
or
i') applying a composition to a substrate S1 and to a substrate S2; and
ii') bonding the applied composition together within an open time of the composition;
wherein the substrate S2 is formed from the same or different material as the substrate S1, and
wherein the composition comprises:
a) at least one aldimine A of Formula (I),

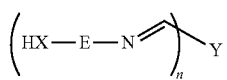

wherein n stands for 2 or 3 or 4,
E either represents a divalent hydrocarbon radical with 3 to 20 C atoms, or together with $R^{11}$ for a trivalent hydrocarbon radical with 3 to 20 C atoms, wherein E optionally contains heteroatoms in the form of ether-oxygen or tertiary amine-nitrogen,
Y represents an n-value organic radical with 6 to 30 C atoms, which optionally contains nitrogen and/or oxygen atoms in the form of tertiary amino groups, or ether, ester, carbonate, amide, urethane or urea groups,
X represents O or S or $N-R^{10}$ or $N-R^{11}$, wherein
$R^{10}$ represents a monovalent hydrocarbon radical with 1 to 20 C atoms, which optionally contains at least one carboxylic acid ester, nitrile, nitro, phosphonic acid ester, sulfonic or sulfonic acid ester group, and
$R^{11}$ together with E represents a trivalent hydrocarbon radical with 3 to 20 C atoms, which optionally contains heteroatoms in the form of ether-oxygen or tertiary amine-nitrogen; and
b) at least one polyisocyanate P.

DETAILED DESCRIPTION

Polyurethane compositions are disclosed, for example, that can be easily processed owing to a sufficiently long open time, that can nevertheless cure quickly and with low odor and thus build up strength quickly, and that can have high tensile strength and a high modulus of elasticity in the cured state.

In addition to at least one polyisocyanate, this composition can contain at least one special aldimine. In addition to several aldimino groups, this aldimine can have several hydroxyl, mercapto or secondary amino groups and can, for example, cross-link the polyisocyanate even in the absence of moisture. With influx of moisture, which can take place at the latest in the application of the composition by air contact, hydrolytic activation of the aldimino groups and their reaction with isocyanate groups that are present can result. A low-odor to odor-free polyaldehyde of low volatility can be released, which can soften the cured composition little or not at all. Based on the special structure of the aldimine, for example, two-component polyurethane compositions are disclosed that on the one hand can have a sufficiently long open time and thus an open time ensuring simple processing, and on the other hand can cure quickly and without bubbles without odor production and very quickly build up strength, and finally, in the cured state, can have pronounced mechanical properties, for example, a high tensile strength and a high modulus of elasticity.

In an exemplary embodiment, a composition is disclosed that contains
a) at least one aldimine A of Formula (I),

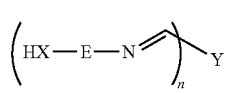

wherein
n stands for 2 or 3 or 4,
E either stands for a divalent hydrocarbon radical with 3 to 20 C atoms, or together with $R^{11}$ for a trivalent hydrocarbon radical with 3 to 20 C atoms, whereby E optionally contains heteroatoms in the form of ether-oxygen or tertiary amine-nitrogen,
Y stands for an n-value organic radical with 6 to 30 C atoms, which optionally has nitrogen and/or oxygen atoms in the form of tertiary amino groups, or ether, ester, carbonate, amide, urethane or urea groups,
X stands for O or S or $N-R^{10}$ or $N-R^{11}$, wherein $R^{10}$ stands for a monovalent hydrocarbon radical with 1 to 20 C atoms, which optionally has at least one carboxylic acid ester, nitrile, nitro, phosphonic acid ester, sulfonic or sulfonic acid ester group, and $R^{11}$ together with E stands for a trivalent hydrocarbon radical with 3 to 20 C atoms, which optionally contains heteroatoms in the form of ether-oxygen or tertiary amine-nitrogen;

and b) at least one polyisocyanate P.

Substance names beginning with "poly," such as polyol, polyisocyanate or polyaldehyde, include substances that formally contain two or more of the functional groups per molecule that occur in their name.

The term "polyisocyanate" comprises compounds with two or more isocyanate groups, regardless of whether these are monomeric diisocyanates, oligomeric polyisocyanates or polymers that have isocyanate groups with a relatively high molecular weight.

The term "primary amino group" includes an amino group in the form of an $NH_2$ group, which is bonded to an organic radical. The term "secondary amino group" includes an amino group in which the nitrogen atom is bonded to two organic radicals, which also can be a common part of a ring. The term "tertiary amino group" includes an amino group in which the nitrogen atom (=tertiary amine-nitrogen) is bonded to three organic radicals, wherein two of these radicals can also be a common part of a ring.

The term "polymer" comprises, on the one hand, a collection of macromolecules that are chemically uniform but different relative to the degree of polymerization, molecular weight, and chain length. The collection can be produced by a polyreaction (polymerization, polyaddition, or polycondensation). The term also comprises derivatives of such a collection of macromolecules from polyreactions. The derivatives can include compounds that are obtained by reactions, such as, for example, additions or substitutions, of functional groups on specified macromolecules, and that can be chemically uniform or chemically non-uniform. In addition, the term also comprises so-called prepolymers, for example, reactive oligomeric prepolymers whose functional groups are involved in the creation of macromolecules.

The term "polyurethane polymer" comprises all polymers that are produced according to the so-called diisocyanate-polyaddition method. This also includes those polymers that are completely or almost free of urethane groups. Examples of polyurethane polymers are polyether-polyurethanes, polyester-polyurethanes, polyether-polyureas, polyureas, polyester-polyureas, polyisocyanurates and polycarbodiimides.

An amine, an aldehyde, and an isocyanate whose amino, aldehyde and isocyanate groups in each case are bonded exclusively to aliphatic, cycloaliphatic or arylaliphatic radicals are referred to as "aliphatic"; correspondingly, these groups are referred to as aliphatic amino, aldehyde and isocyanate groups.

An amine, an aldehyde and an isocyanate, whose amino, aldehyde and isocyanate groups in each case are bonded to an aromatic radical, are referred to as "aromatic"; correspondingly, these groups are referred to as aromatic amino, aldehyde and isocyanate groups.

The composition can contain at least one aldimine A of Formula (I),

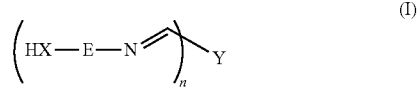

wherein X can stand for O, thus for an oxygen atom.

As aldimine A of Formula (I), an aldimine A1 of Formula (II) can be used,

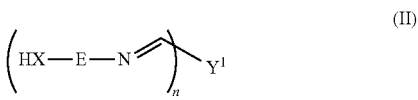

wherein $Y^1$ stands for an n-value, substituted or unsubstituted aryl or heteroaryl radical, which has a ring size of 5 to 8, for example, 6, atoms;

and n, X and E have the already mentioned meanings.

As aldimine A of Formula (I), an aldimine A2 of Formula (III) can be used,

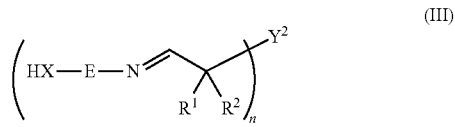

wherein $R^1$ and $R^2$ either independently of one another in each case stand for a monovalent hydrocarbon radical with 1 to 12 C atoms, or together stand for a divalent hydrocarbon radical with 4 to 12 C atoms, which is part of an optionally substituted, carbocyclic ring with 5 to 8, for example, 6, C atoms;

$Y^2$ stands for an n-value organic radical with 1 to 24 C atoms, which optionally has nitrogen and/or oxygen atoms in the form of tertiary amino groups, or ether, ester, carbonate, amide, urethane or urea groups;

and n, X and E have the already mentioned meanings.

The aldimines A2 of Formula (III) and/or the aldimines A1 of Formula (II) can be used.

As aldimine A of Formula (I), or aldimine A2 of Formula (III), aldimines A3 of Formula (III a) can be used,

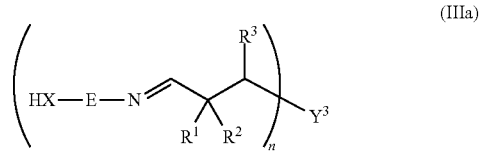

wherein $R^3$ stands for a hydrogen atom or for an alkyl, cycloalkyl, arylalkyl or alkoxycarbonyl radical with 1 to 12 C atoms;

$Y^3$ stands for an n-value radical that is selected from

[chemical structures showing various radicals containing N, Z¹, Z², Z³, R⁴, R⁵, R⁶, R⁷, R⁸ groups with carbonyl, ester, carbamate and urea functionalities]

wherein
m stands for 0 or 1;
$Z^1$ either stands for a carbonyl group or for an alkylene radical with 2 to 15 C atoms, which optionally has at least one ether group;
$Z^2$ stands for a divalent hydrocarbon radical with 1 to 15 C atoms, which optionally has at least one ether, carbonyl or carboxyl group;
$Z^3$ stands for an n-value hydrocarbon radical with 2 to 15 C atoms, which optionally has at least one ether or carbonyl group;
$R^4$ stands for an alkyl, cycloalkyl or arylalkyl radical with 1 to 20 C atoms;
$R^5$ and $R^6$ either
  independently of one another in each case stand for an alkyl, cycloalkyl or arylalkyl radical with 1 to 12 C atoms,
  or, for the case that $Z^1$ stands for a carbonyl group, independently of one another in each case stand for a hydrogen atom or for an alkyl, cycloalkyl or arylalkyl radical with 1 to 12 C atoms;
  or together for an alkylene radical with 2 to 20 C atoms, which together with N—$Z^1$—N forms a 5- to 12-membered ring and optionally has at least one ether group;
$R^7$ either
  stands for an alkyl, cycloalkyl or arylalkyl radical with 1 to 15 C atoms;
  or, for the case that $Z^1$ stands for a carbonyl group, for a hydrogen atom or for an alkyl, cycloalkyl or arylalkyl radical with 1 to 15 C atoms;
and $R^8$ stands for a hydrogen atom or for an alkyl, cycloalkyl or arylalkyl radical with 1 to 8 C atoms;
and n, X, E, $R^1$ and $R^2$ have the already mentioned meanings.

Dotted lines in the formulas represent the bond between a substituent and the related molecule radical.
$R^1$ and $R^2$ can stand for a methyl radical.
$R^3$ can stand for a hydrogen atom.
$R^4$ can stand for an alkyl, cycloalkyl or arylalkyl radical with 6 to 20 C atoms.
$R^5$ and $R^6$, together with N—$Z^1$—N, can form a piperazine radical, or an imidazolidin-2-one radical, or a hexahydropyrimidin-2-one radical, which optionally is substituted.
For the case that $Z^1$ stands for carbonyl, $R^5$ and $R^6$ in addition can stand for a methyl radical or for a hydrogen atom or for a radical $R^{13}$ of Formula (IX).
$Y^3$ can stand for the radical

[chemical structure showing N-Z¹-N with R⁵ and R⁶ substituents]

The aldimines A of Formula (I) can be low-odor or odor-free substances.
The aldimines A2 of Formula (III) or the aldimines A3 of Formula (III a) can be odor-free substances.
A "low-odor" substance includes a substance whose odor is perceptible to, for example, can be smelled by, humans only to a slight extent; it thus does not have an intense odor, such as, for example, formaldehyde, acetaldehyde, isobutyraldehyde, or solvents such as acetone, methyl ethyl ketone or methyl isobutyl ketone, and whereby this slight odor is not considered to be unpleasant or repellent by most humans.
An "odorless" substance includes a substance that most humans cannot smell and that thus has substantially no perceptible odor.
An aldimine A of Formula (I) can be available from the reaction of at least one amine B of Formula (IV) with at least one polyaldehyde ALD of Formula (V).

$$HX-E-NH_2 \qquad (IV)$$

$$\left(O\!\!=\!\!\!\diagup\right)_n\!Y \qquad (V)$$

In this connection, n, X, E and Y have the already mentioned meanings.
The reaction between the amine B of Formula (IV) and the polyaldehyde ALD of Formula (V) can be carried out in a condensation reaction while being cleaved with water. Such condensation reactions are described, for example, in Houben-Weyl, "Methoden der organischen Chemie [Methods of Organic Chemistry]," Vol. XI/2, p. 73 ff. The aldehyde groups of the polyaldehyde can be used stoichiometrically or in stoichiometric excess relative to the primary amino groups of the amine B. Such condensation reactions can be performed in the presence of a solvent, wherein the water that is produced during the reaction can be removed azeotropically. For the production of an aldimine A of Formula (I), however, a production method without using solvents can be used, whereby the water that is formed upon condensation can be removed directly from the reaction mixture by applying a vacuum. Because of the solvent-free production, for example, distilling-off of the solvent after production is unnecessary, which can simplify the production process. Moreover, the aldimine can be free of solvent residues, which could cause an objectionable odor.

As amine B of Formula (IV), compounds that have both a primary amino group and a reactive group in the form of a hydroxyl, mercapto or secondary amino group can be used. The following can be used as amine B:

Hydroxyamines, such as, for example, 2-aminoethanol, 2-amino-1-propanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethyl-cyclohexanol; a derivative of glycol that carries a primary amino group such as, for example, diethylene glycol, dipropylene glycol, dibutylene glycol and higher oligomers and polymers of these glycols, for example, 2-(2-aminoethoxy)-ethanol, 2-(2-(2-aminoethoxy)ethoxy)ethanol, α-(2-hydroxymethylethyl)-ω-(2-aminomethylethoxy)-poly(oxy(methyl-1,2-ethanediyl)); a derivative of polyalkoxylated trivalent or higher-value alcohols that carries a hydroxyl group and a primary amino group; products from simple cyanoethylation and subsequent hydrogenation of glycols, for example, 3-(2-hydroxyethoxy)-propylamine, 3-(2-(2-hydroxyethoxy)-ethoxy)-propylamine and 3-(6-hydroxyhexyloxy)-propylamine;

Aliphatic mercaptoamines, such as, for example, 2-aminoethanethiol (cysteamine), 3-aminopropanethiol, 4-amino-1-butanethiol, 6-amino-1-hexanethiol, 8-amino-1-octanethiol, 10-amino-1-decanethiol and 12-amino-1-dodecanethiol;

Compounds with one primary and one secondary aliphatic amino group each, such as, for example, N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethyl-piperidine, 3-(4-aminobutyl)-piperidine, N-(2-aminoethyl)piperazine, diamines from cyanoethylation or cyanobutylation and subsequent hydrogenation of primary monoamines, such as, for example, N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, and fatty diamines such as N-coco alkyl-1,3-propanediamine, N-oleyl-1,3-propanediamine, N-soya alkyl-1,3-propanediamine, N-tallowalkyl-1,3-propanediamine and N—($C_{16-22}$-alkyl)-1,3-propanediamine, as they are available, for example, under the trade name Duomeen® by Akzo Nobel; as well as the products from the Michael-like addition of aliphatic primary diamines with acrylonitrile, maleic or fumaric acid diesters, citraconic acid diesters, acrylic and methacrylic acid esters, acrylic and methacrylic acid amides and itaconic acid diesters, reacted in the molar ratio 1:1.

Hydroxy- or mercaptoamines which can be used include, for example, those in which the primary amino group is separated from the hydroxyl or mercapto group by a chain of at least 5 atoms, or by a ring, for example, 5-amino-1-pentanol, 6-amino-1-hexanol and higher homologs thereof, 4-(2-aminoethyl)-2-hydroxyethylbenzene, 3-aminomethyl-3,5,5-trimethyl-cyclohexanol, 2-(2-aminoethoxy)-ethanol, triethyleneglycol-monoamine and higher homologs thereof, 3-(2-hydroxyethoxy)-propylamine, 3-(2-(2-hydroxyethoxy)-ethoxy)-propylamine and 3-(6-hydroxyhexyloxy)-propylamine.

The amine B can be selected from 5-amino-1-pentanol, 6-amino-1-hexanol or higher homologs thereof, 4-(2-aminoethyl)-2-hydroxyethylbenzene, 3-aminomethyl-3,5,5-trimethyl-cyclohexanol, 2-(2-aminoethoxy)-ethanol, triethylene glycol monoamine or higher homologs thereof, 3-(2-hydroxyethoxy)-propylamine, 3-(2-(2-hydroxyethoxy)-ethoxy)-propylamine, 3-(6-hydroxyhexyloxy)-propylamine, N-methyl-1,3-propanediamine, N-ethyl-1,3-propanediamine, N-butyl-1,3-propanediamine, N-(2-ethylhexyl)-1,3-propanediamine, N-dodecyl-1,3-propanediamine, N-cyclohexyl-1,3-propanediamine, N-coco alkyl-1,3-propanediamine, N-oleyl-1,3-propanediamine, N-soya alkyl-1,3-propanediamine, N-tallowalkyl-1,3-propanediamine and N—($C_{16-22}$-alkyl)-1,3-propanediamine.

5-Amino-1-pentanol and 2-(2-aminoethoxy)-ethanol can be employed as amine B. 2-(2-Aminoethoxy)-ethanol can be employed.

In an exemplary embodiment, aliphatic or cycloaliphatic polyaldehydes, such as, for example, suberic aldehyde, azelaic aldehyde, sebacic aldehyde, 1,12-dodecane dialdehyde, hexahydrophthalaldehyde, hexahydroisophthalaldehyde, hexahydroterephthalaldehyde, octahydro-4,7-methano-1H-indenedicarbaldehyde, 3,6,9-trioxaundecane-1,1'-dial and higher homologs thereof can be suitable as polyaldehyde ALD of Formula (V).

Aromatic polyaldehydes ALD1 of Formula (VI) can be suitable as polyaldehyde ALD of Formula (V).

In this connection, n and $Y^1$ have the already mentioned meanings.

Suitable polyaldehydes ALD1 include, for example, aromatic dialdehydes, such as, for example, phthalaldehyde, isophthalaldehyde, terephthalaldehyde, 9,10-anthracenedicarbaldehyde as well as 2,3-naphthalenedicarboxaldehyde and isomers thereof.

Starting from polyaldehydes ALD1, exemplary aldimines A1 of Formula (II) are available.

In addition, polyaldehydes ALD2 of Formula (VII) can be suitable as polyaldehyde ALD of Formula (V).

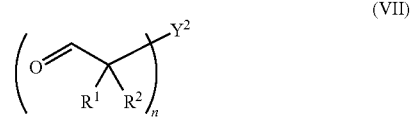

In this connection, n, $R^1$, $R^2$ and $Y^2$ have the already mentioned meanings.

Starting from polyaldehydes ALD2, exemplary aldimines A2 of Formula (III) are available.

As polyaldehyde ALD2 of Formula (VII), for example, 2,2,6,6-tetramethylheptane-1,7-dial, 2,2,7,7-tetramethyloctane-1,8-dial as well as 1,3- and 1,4-bis-(4,4-dimethyl-5-oxo-2-pentyl)-benzene can be suitable.

As polyaldehyde ALD2 of Formula (VII), polyaldehydes ALD3 of Formula (VIII) can be suitable.

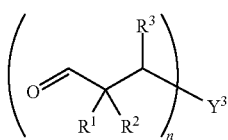

(VIII)

In this connection, n, $R^1$, $R^2$, $R^3$ and $Y^3$ have the already mentioned meanings.

In one embodiment, a polyaldehyde ALD3a of Formula (VIII a) can be suitable as polyaldehyde ALD3 of Formula (VIII).

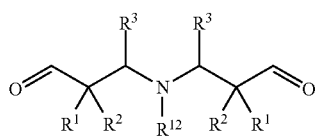

(VIIIa)

In this connection, $R^{12}$ either stands for $R^4$ or for a radical $R^{13}$ of Formula (IX), and $R^1$, $R^2$, $R^3$ and $R^4$ have the already mentioned meanings.

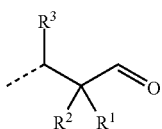

(IX)

A polyaldehyde ALD3a of Formula (VIII a) can be used as a product of a Mannich reaction or an α-aminoalkylation that is analogous to the Mannich reaction, as it is known from the technical literature; it can therefore also be referred to as a Mannich base. An aldehyde Y1 of Formula (X), an aldehyde Y2 of Formula (XI), and a compound C1 of Formula (XII a) can be reacted with water being separated off to form a polyaldehyde ALD3a of Formula (VIII a).

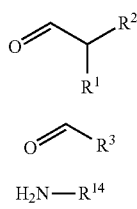

(X)

(XI)

(XII a)

In this connection, $R^{14}$ either stands for a hydrogen atom or for $R^4$; and $R^1$, $R^2$, $R^3$ and $R^4$ have the already mentioned meanings.

This reaction can be run with the free reagents Y1, Y2 and C1 according to Formulas (X), (XI) and (XII a), or the reagents can be used partially or completely in derivatized form. In an exemplary embodiment, the reaction is run with all reagents in free form as a single-pot reaction, and the polyaldehyde ALD3a can be purified by distillation after the reaction has been completed. In an exemplary embodiment, no organic solvents are used.

As aldehyde Y1 of Formula (X), for example, the following aldehydes can be suitable: isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde and diphenylacetaldehyde. Isobutyraldehyde can be used.

As aldehyde Y2 of Formula (XI), for example, the following aldehydes can be suitable: formaldehyde, acetaldehyde, propionaldehyde, butyraldehyde, isobutyraldehyde, phenylacetaldehyde and glyoxylic acid ester, for example, glyoxylic acid ethyl ester. Formaldehyde can be used.

As compound C1 of Formula (XII a), primary aliphatic amines, for example, the following, can be suitable in an exemplary embodiment: methylamine, ethylamine, propylamine, isopropylamine, butylamine, isobutylamine, sec-butylamine, hexylamine, cyclohexylamine, octylamine, 2-ethyl-1-hexylamine, benzylamine, 1- or 2-phenylethylamine, decylamine, dodecylamine, tetradecylamine, hexadecylamine, octadecylamine, eicosylamine, as well as fatty amines derived from natural fatty acid mixtures, such as, for example, coco alkylamine, $C_{16}$-$C_{22}$-alkylamine, soya alkylamine, oleylamine and tallow alkylamine, available, for example, under the trade names Armeen® (by Akzo Nobel) or Rofamin® (by Ecogreen Oleochemicals).

As compound C1 of Formula (XII a), ammonia can be suitable in an exemplary embodiment.

In the case of ammonia as compound C1, 3 mol each of the aldehydes Y1 and Y2 can be reacted per mol of ammonia, whereby a polyaldehyde ALD3a with three aldehyde groups can be formed, while in the case of a primary aliphatic amine as compound C1 per mol of amine, 2 mol each of aldehydes Y1 and Y2 can be reacted, and a polyaldehyde ALD3a can be formed with two aldehyde groups.

As polyaldehydes ALD3 of Formula (VIII), polyaldehydes ALD3b of Formula (VIII b) can be suitable in another embodiment.

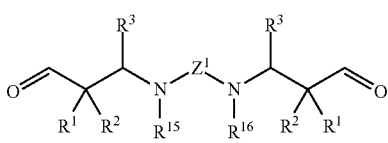

(VIII b)

In this connection, in one embodiment, $R^{15}$ stands for $R^5$ and $R^{16}$ stands for $R^6$; in another embodiment, $R^{15}$ stands for $R^7$ and $R^{16}$ stands for $R^{13}$; in another embodiment, $R^{15}$ and $R^{16}$ each stand for a radical $R^{13}$; and $Z^1$, $R^1$, $R^2$, $R^3$, $R^5$, $R^6$, $R^7$ and $R^{13}$ have the already mentioned meanings.

A polyaldehyde ALD3b of Formula (VIII b) can be available in the same way as described for a polyaldehyde ALD3a of Formula (VIII a), but instead of a compound C1 of Formula (XII a), a compound C2 of Formula (XII b) can be used.

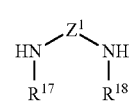

(XII b)

In this connection, in one exemplary embodiment, $R^{17}$ stands for $R^5$ and $R^{18}$ stands for $R^6$; in another exemplary embodiment, $R^{17}$ stands for $R^7$ and $R^{18}$ stands for a hydrogen atom; in another exemplary embodiment, $R^{17}$ and $R^{18}$ each stand for a hydrogen atom; and $Z^1$, $R^5$, $R^6$ and $R^7$ have the already mentioned meanings.

As compound C2, the following can be suitable in an exemplary embodiment: polyamines with two secondary amino groups, such as, for example, piperazine, 2,5- and 2,6-dimethylpiperazine, 1,7-dioxa-4,10-diazacyclododecane, N,N'-dibutylethylenediamine; N,N'-di-tert-butylethylenediamine, N,N'-diethyl-1,6-hexanediamine, 1-(1-methylethyl-amino)-3-(1-methylethyl-aminomethyl)-3,5,5-trimethylcyclohexane (Jefflink® 754 by Huntsman), N4-cyclohexyl-2-methyl-N2-(2-methylpropyl)-2,4-pentanediamine, N,N'-dialkyl-1,3-xylylenediamine, bis-(4-(N-alkylamino)-cyclohexyl)-methane, 4,4'-trimethylene-dipiperidine and N-alkylated polyetheramines, for example Jeffamine®-SD-231 (by Huntsman); and in addition, disubstituted ureas, for example, N,N'-dialkylureas such as N,N'-dimethylurea, N,N'-diethylurea, N,N'-dibutylurea, for example, cyclic ureas such as imidazolidin-2-one and hexahydropyrimidin-2-one.

In an exemplary embodiment, 2 mol each of the aldehydes Y1 and Y2 can be used per mol of compound C2, so that polyaldehydes ALD3b of Formula (VIII b) are formed with two aldehyde groups.

As compound C2, the following can be suitable in an exemplary embodiment: polyamines with a secondary and a primary amino group, such as, for example, N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethyl-piperidine, 3-(4-aminobutyl)-piperidine, N-(2-aminoethyl)piperazine, diamines from cyanoethylation or cyanobutylation and subsequent hydrogenation of primary monoamines, such as, for example, N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, and fatty diamines such as N-coco alkyl-1,3-propanediamine, as they are available, for example, under the trade name Duomeen® by Akzo Nobel; as well as the products from the Michael-like addition of aliphatic primary diamines with acrylonitrile, maleic or fumaric acid diesters, citraconic acid diesters, acrylic and methacrylic acid esters, acrylic and methacrylic acid amides and itaconic acid diesters, reacted in the molar ratio 1:1. In an exemplary embodiment, 3 mol each of the aldehydes Y1 and Y2 can be used per mol of the compound C2, so that polyaldehydes ALD3b of Formula (VIII b) are formed with three aldehyde groups.

In an exemplary embodiment, monosubstituted ureas, for example, N-alkylureas, such as N-methylurea, N-ethylurea or N-butylurea, can be suitable as compound C2. In an exemplary embodiment, 2 or 3 mol of the aldehydes Y1 and Y2 can be used per mol of compound C2, so that polyaldehydes ALD3b of Formula (VIII b) are formed with two or three aldehyde groups.

In an exemplary embodiment, the following can be suitable as compound C2: polyamines with two primary amino groups, such as, for example, ethylenediamine, 1,2-propanediamine, 1,3-propanediamine, 2-methyl-1,2-propanediamine, 2,2-dimethyl-1,3-propanediamine, 1,3-butanediamine, 1,4-butanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2,4- and 2,4,4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- and 1,4-diaminocyclohexane, bis-(4-aminocyclohexyl)-methane ($H_{12}$-MDA), bis-(4-amino-3-methylcyclohexyl)-methane, 1-amino-3-aminomethyl-3,5,5-trimethylcyclohexane (=isophoronediamine or IPDA), 2- and 4-methyl-1,3-diaminocyclohexane and mixtures thereof, 1,3- and 1,4-bis-(aminomethyl)cyclohexane, 2,5(2,6)-bis-(aminomethyl)-bicyclo[2.2.1]-heptane (NBDA), 3(4),8(9)-bis-(aminomethyl)-tricyclo[5.2.1.0$^{2,6}$] decane, 1,4-diamino-2,2,6-trimethylcyclohexane (TMCDA), 1,8-menthanediamine, 3,9-bis-(3-aminopropyl)-2,4,8,10-tetraoxaspiro[5.5]undecane, 1,3- and 1,4-xylylenediamine, as well as ether-group-containing aliphatic diamines, for example, bis-(2-aminoethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine as well as short-chain polyoxyalkylene-diamines, which represent products from the amination of polyoxyalkylene-diols and are available, for example, under the name Jeffamine® (by Huntsman), under the name polyetheramine (by BASF) or under the name PC Amine® (by Nitroil); especially suitable polyoxyalkylene-diamines are Jeffamine® D-230, Jeffamine® XTJ-511, Jeffamine® XTJ-568, polyetheramine D 230 and PC Amine® DA 250.

In an exemplary embodiment, 4 mol each of aldehydes Y1 and Y2 can be used per mol of compound C2, so that polyaldehydes ALD3b of Formula (VIII b) are formed with four aldehyde groups.

In an exemplary embodiment, urea can be suitable as compound C2. In an exemplary embodiment, 2 or 3 or 4 mol of aldehydes Y1 and Y2 can be used per mol of urea, so that polyaldehydes ALD3b of Formula (VIII b) are formed with two or three or four aldehyde groups.

The compound C2 of Formula (XII b) can be selected from piperazine, 2,5- and 2,6-dimethylpiperazine, N,N'-dimethylurea, imidazolidin-2-one, hexahydropyrimidin-2-one and urea.

In an exemplary embodiment, polyaldehydes ALD3c of Formula (VIII c) can be suitable as polyaldehydes ALD3 of Formula (VIII).

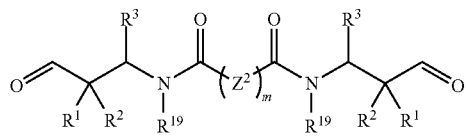

(VIII c)

In this connection, the radicals $R^{19}$, in each case independently of one another, either stand for $R^8$ or for $R^{13}$; and m, $Z^2$, $R^1$, $R^2$, $R^3$, $R^8$ and $R^{13}$ have the already mentioned meanings.

In an exemplary embodiment, a polyaldehyde ALD3c of Formula (VIII c) can be available in the same way as described for a polyaldehyde ALD3a of Formula (VIII a), but instead of a compound C1 of Formula (XII a), a diamide with two or three or four amide-hydrogen atoms can be used.

A production method with an intermediate product ZW1 of Formula (XIII) can be used for the production of a polyaldehyde ALD3c of Formula (VIII c).

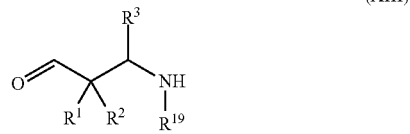

(XIII)

In this connection, $R^1$, $R^2$, $R^3$ and $R^{19}$ have the already mentioned meanings.

An intermediate product ZW1 of Formula (XIII) can be available in the same way as described for a polyaldehyde ALD3a of Formula (VIII a), whereby the reaction between the compound C1 of Formula (XII a) and the two aldehydes Y1 and Y2 can be carried out in such a way that the amine-hydrogen atoms are used hyperstoichiometrically relative to the aldehyde groups. Then, the intermediate product ZW1 can be reacted with a dicarboxylic acid, for example, in the form of a dicarboxylic acid dichloride or diester, or with a tetracarboxylic acid dianhydride to form the corresponding diamide, whereby a polyaldehyde ALD3c of Formula (VIII c) can be formed. Suitable dicarboxylic acids include, for example, oxalic acid, malonic acid, succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydroterephthalic acid, methylhexahydrophthalic acid, 3,6,9-trioxaundecanedioic acid, and higher homologs thereof, phthalic acid, isophthalic acid, and terephthalic acid, as well as dichlorides and diesters, for example, methyl and ethyl esters, of the above-mentioned dicarboxylic acids. Suitable tetracarboxylic acid dianhydrides include, for example, 1,2,4,5-benzenetetracarboxylic acid dianhydride, 1,8,4,5-naphthalenetetracarboxylic acid dianhydride, 3,4,3',4'- and 2,3,3',4'-biphenyltetracarboxylic acid dianhydride, 3,4,3',4'- and 2,3,3',4'-benzophenonetetracarboxylic acid-dianhydride, oxydiphthalic acid dianhydride and hexahydro-4,8-ethano-1H,3H-benzo[1,2-c:4,5-c']difuran-1,3,5,7-tetrone.

In an exemplary embodiment, polyaldehydes ALD3d of Formula (VIII d) can be suitable as polyaldehydes ALD3 of Formula (VIII).

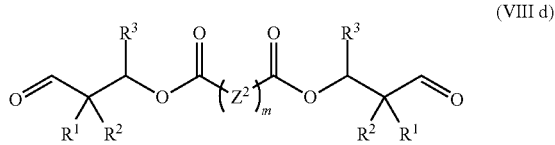

(VIII d)

In this connection, m, $Z^2$, $R^1$, $R^2$ and $R^3$ have the already mentioned meanings.

Polyaldehydes ALD3d of Formula (VIII d) can represent, for example, diesters of 2,2-disubstituted 3-hydroxyaldehydes and dicarboxylic acids. The 2,2-disubstituted 3-hydroxyaldehydes in turn can represent products from aldol reactions, for example, crossed aldol reactions, between primary or secondary aliphatic aldehydes, for example, formaldehyde, and secondary aliphatic, secondary cycloaliphatic, or secondary arylaliphatic aldehydes, such as, for example, isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde (hydratropaldehyde) or diphenylacetaldehyde. Suitable 2,2-disubstituted 3-hydroxyaldehydes can include, for example, 2,2-dimethyl-3-hydroxypropanal, 2-hydroxymethyl-2-methyl-butanal, 2-hydroxymethyl-2-ethyl-butanal, 2-hydroxymethyl-2-methylpentanal, 2-hydroxymethyl-2-ethylhexanal, 1-hydroxymethyl-cyclopentanecarboxaldehyde, 1-hydroxymethyl-cyclohexane-carboxaldehyde, 1-hydroxymethyl-cyclohex-3-enecarboxaldehyde, 2-hydroxymethyl-2-methyl-3-phenyl-propanal, 3-hydroxy-2-methyl-2-phenyl-propanal and 3-hydroxy-2,2-diphenyl-propanal. Suitable exemplary dicarboxylic acids were already described with the polyaldehydes ALD3c. The production of polyaldehydes ALD3d can be carried out, for example, by direct esterification of the above-mentioned hydroxyaldehydes with the above-mentioned dicarboxylic acids.

In an exemplary, embodiment, polyaldehydes ALD3e of Formula (VIII e) can be suitable as polyaldehydes ALD3 of Formula (VIII).

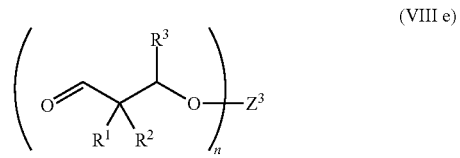

(VIII e)

In this connection, n, $Z^3$, $R^1$, $R^2$ and $R^3$ have the already mentioned meanings.

Polyaldehydes ALD3e of Formula (VIII e) can represent, for example, ethers of 2,2-disubstituted 3-hydroxyaldehydes and divalent and multivalent alcohols or phenols. Suitable exemplary 2,2-disubstituted 3-hydroxyaldehydes were already described in connection with the polyaldehydes ALD3d.

Suitable divalent and multivalent alcohols or phenols can include, for example, 1,3-propylene glycol, 1,2-propylene glycol, 1,4-butylene glycol, 1,6-hexanediol, 1,8-octanediol, 1,10-decanediol, neopentyl glycol, diethylene glycol, triethylene glycol, the isomeric dipropylene glycols and tripropylene glycols, hydrogenated bisphenol A, 1,1,1-trimethylolethane, 1,1,1-trimethylolpropane, glycerol, pentaerythritol, low-molecular alkoxylating products of the above-mentioned divalent and multivalent alcohols, resorcinol, bisphenol A, bisphenol F, bis-(4-hydroxy-3-methylphenyl)-methane, 4,4'-dihydroxydiphenyl (DOD), 4,4'-dihydroxybenzophenone, 1,5-dihydroxy-naphthalene and bis-(4-hydroxyphenyl)-ether. The production of polyaldehydes ALD3e can be carried out, for example, by crossed etherification between the above-mentioned hydroxyaldehydes and the above-mentioned divalent and multivalent alcohols or phenols. Another method for production of polyaldehydes ALD3e, described in, for example, U.S. Pat. No. 3,676,500, involves thermally induced ring opening by suitable meta-dioxanes.

In an exemplary embodiment, polyaldehydes ALD3f of Formula (VIII f) can be suitable as polyaldehydes ALD3 of Formula (VIII).

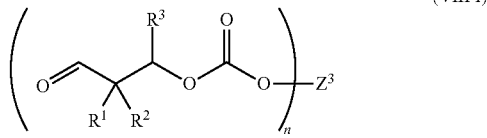
(VIII f)

In this connection, n, $Z^3$, $R^1$, $R^2$ and $R^3$ have the already mentioned meanings.

Polyaldehydes ALD3f of Formula (VIII f) can represent, for example, dicarbonates of 2,2-disubstituted 3-hydroxyaldehydes and divalent and multivalent alcohols or phenols. Suitable exemplary 2,2-disubstituted 3-hydroxyaldehydes were already described in connection with the polyaldehydes ALD3d and suitable exemplary divalent and multivalent alcohols or phenols were described in connection with the polyaldehydes ALD3e. The production of polyaldehydes ALD3f can be carried out, for example, by reaction of the above-mentioned hydroxyaldehydes with chloroformic acid esters of the above-mentioned divalent and multivalent alcohols or phenols, such as, for example, ethylenebis-chloroformate or 1,6-hexylenebis-chloroformate.

In another embodiment, polyaldehydes ALD3g of Formula (VIII g) can be suitable as polyaldehydes ALD3 of Formula (VIII).

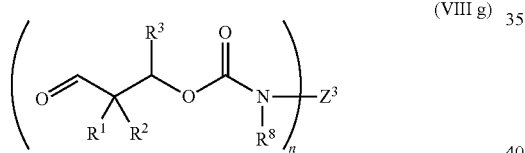
(VIII g)

In this connection, n, $Z^3$, $R^1$, $R^2$, $R^3$ and $R^8$ have the already-mentioned meanings.

Polyaldehydes ALD3g of Formula (VIII g) can represent, for example, diurethanes of 2,2-disubstituted 3-hydroxyaldehydes and diamines. The production of polyaldehydes ALD3g can be carried out, for example, by reaction of the 2,2-disubstituted 3-hydroxyaldehydes, already described in connection with the polyaldehydes ALD3d, with polyisocyanates, optionally followed by an alkylation step. For this reaction, suitable polyisocyanates are, for example, the polyisocyanates that are described further back in this document as polyisocyanates PI.

In an exemplary embodiment, polyaldehydes ALD3h of Formula (VIII h) can be suitable as polyaldehydes ALD3 of Formula (VIII).

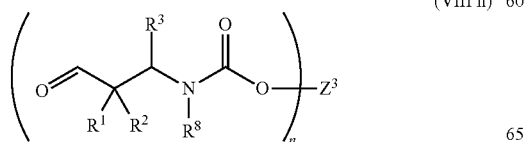
(VIII h)

In this connection, n, $Z^3$, $R^1$, $R^2$, $R^3$ and $R^8$ have the already mentioned meanings.

Polyaldehydes ALD3h of Formula (VIII h) are available, for example, from the reaction of the already described intermediate products ZW1 of Formula (XIII), in which $R^{19}$ stands for $R^8$, with dicarbonates, as they were already mentioned for the production of a polyaldehyde ALD3f of Formula (VIII f), or for example, from the reaction with dichlorides of such dicarbonates, as they are shown in Formula (XIV), such as, for example, ethylenebis-chloroformate or 1,6-hexylenebis-chloroformate.

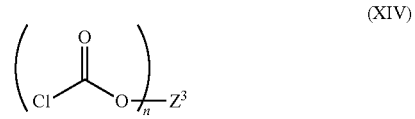
(XIV)

In this connection, n and $Z^3$ have the already mentioned meanings.

In an exemplary embodiment, polyaldehydes ALD3l of Formula (VIII i) can be suitable as polyaldehydes ALD3 of Formula (VIII).

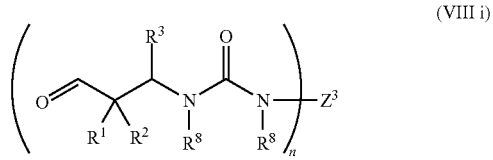
(VIII i)

In this connection, n, $Z^3$, $R^1$, $R^2$, $R^3$ and $R^8$ have the already mentioned meanings.

Polyaldehydes ALD3i of Formula (VIII i) are available, for example, from the reaction of the already described intermediate products ZW1 of Formula (XIII), in which $R^{19}$ stands for $R^8$, with polyisocyanates, optionally followed by an alkylation step. Polyisocyanates that can be suitable for this reaction are the polyisocyanates that are described further back in this document as polyisocyanates PI.

As polyaldehyde ALD of Formula (V), polyaldehydes ALD1 of Formula (VI) and ALD2 of Formula (VII) can be used. Polyaldehydes ALD3 of Formula (VIII) can be used, and of these, polyaldehydes ALD3b of Formula (VIII b) can be used.

In an exemplary embodiment, the polyaldehydes ALD1 and the polyaldehydes ALD2 do not have any hydrogen atom in α-position in the carbonyl-C atom. As a result, their aldehyde groups cannot tautomerize to form enol groups and are thus unreactive to isocyanate groups.

The polyaldehydes ALD2, for example, are odorless.

An exemplary production method for aldimines A3 of Formula (III a), in which X stands for O or S and $Y^3$ stands for one of the radicals,

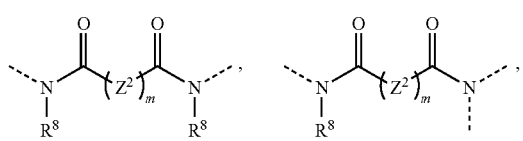

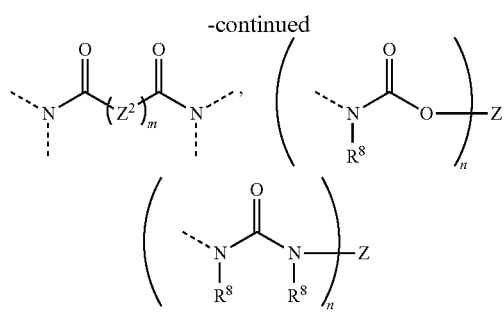

or involves an intermediate product ZW2 of Formula (XV).

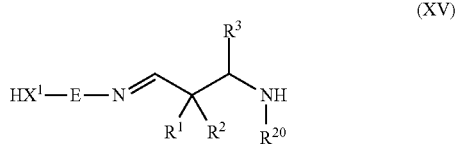

In this connection, $X^1$ stands for O or S, $R^{20}$ stands for $R^8$ or for a radical $R^{21}$ of Formula (XVI); and E, $R^1$, $R^2$, $R^3$ and $R^8$ have the already mentioned meanings.

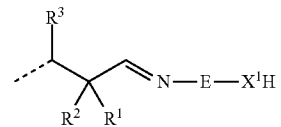

Instead of the intermediate product ZW1, the intermediate product ZW2 can be reacted either with at least one dicarboxylic acid, for example, in the form of a dicarboxylic acid dichloride or diester, or with at least one tetracarboxylic acid dianhydride, or with at least one dichloride of a dicarbonate of Formula (XIV), or with at least one polyisocyanate to form the corresponding aldimine A3 directly.

The intermediate product ZW2 can be available, for example, by the reaction of a corresponding intermediate product ZW1, in which X stands for O or S, with at least one amine B of Formula (IV), whereby the amine B is used stoichiometrically with reference to the aldehyde groups of the intermediate product ZW1.

As mentioned, the aldimines A of Formula (I) are low-odor or, for example, odorless substances. They can have n HX groups in the form of hydroxyl, secondary amino or mercapto groups. In addition, they can have n aldimino groups. They can have a long shelf life under proper conditions. If moisture gains access, their aldimino groups can hydrolyze formally to form amino groups via intermediate stages, whereby the corresponding polyaldehydes ALD of Formula (V), used for the production of aldimines, can be released. Since this hydrolysis reaction can be reversible, and the chemical equilibrium lies clearly on the aldimine side, it can be assumed from this that in the absence of compounds that are reactive to amines, for example, isocyanates, only a portion of the aldimino groups partially or completely hydrolyzes. In turn, the polyaldehydes ALD of Formula (V) that are released in the hydrolysis of the aldimines A can be low-odor or odorless, owing to their relatively high molecular weight and their chemical structure.

Exemplary aldimines A1 of Formula (II) and A2 of Formula (III) can have aldimino groups that cannot tautomerize to form enamino groups. For use together with isocyanate groups, such aldimino groups can represent especially well protected amino groups.

Exemplary aldimines A2 of Formula (III) can be new compounds with advantageous properties. During their hydrolysis, polyaldehydes A2 of Formula (VII) can be released, which can be low-odor or odorless, and can largely remain in the cured composition because of their low volatility. During their hydrolysis, exemplary aldimines A3 of Formula (III a) can release polyaldehydes ALD3 of Formula (VIII). In addition to aldehyde groups, the latter can have additional functional groups, which can be able to form hydrogen bridge-bonds.

Since the polyaldehydes ALD can have two to four aldehyde groups, they can have a relatively low aldehyde equivalent weight despite their size. As a result, the absolute amount of the released polyaldehyde ALD in the cured composition can remain relatively low in % by weight. In connection with the relatively high viscosity or the solid aggregate state of many of the polyaldehydes ALD, this can result in that the polyaldehydes ALD exert no or only a little softening effect on the composition.

In addition, the composition can contain at least one polyisocyanate P.

In an exemplary embodiment, a polyisocyanate PI in the form of a monomeric di- or triisocyanate or an oligomer of a monomeric diisocyanate or a derivative of a monomeric diisocyanate can be suitable as a polyisocyanate P.

As monomeric di- or triisocyanates, for example, the following can be suitable: 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any mixtures of these isomers (HTDI or $H_6TDI$), 1-isocyanato-3,3,5-trimethyl-5-isocyanatomethyl-cyclohexane (=isophoronediisocyanate or IPDI), perhydro-2,4'- and -4,4'-diphenylmethane diisocyanate (HMDI or $H_{12}MDI$), 1,4-diisocyanato-2,2,6-trimethylcyclohexane (TMCDI), 1,3- and 1,4-bis-(isocyanatomethyl)-cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)-naphthalene, dimer- and trimer fatty acid isocyanates such as 3,6-bis-(9-isocyanatononyl)-4,5-di-(1-heptenyl)-cyclohexene (dimeryl diisocyanate), α,α,α',α',α'',α''-hexamethyl-1,3,5-mesitylene-triisocyanate, 2,4- and 2,6-toluoylenediisocyanate and any mixtures of these isomers (TDI), 4,4'-, 2,4'- and 2,2'-diphenylmethane diisocyanate and any mixtures of these isomers (MDI), mixtures that contain MDI and MDI homologs (MDI or PMDI polymers), 1,3- and 1,4-phenylene diisocyanate, 2,3,5,6-tetramethyl-1,4-diisocyanatobenzene, naphthalene-1,5-diisocyanate (NDI), 3,3'-dimethyl-4,4'-diisocyanatodiphenyl (TODI), dianisidine diisocyanate (DADI), 1,3,5-tris-(isocyanatomethyl)-benzene, tris-(4-isocyanatophenyl)-methane and tris-(4-isocyanatophenyl)-thiophosphate.

As polyisocyanate PI, the following can be suitable: oligomers or derivatives of monomeric diisocyanates, for example, of HDI, IPDI, TDI and MDI. Commercially available types include, for example, HDI biurets, for example as Desmodur® N 100 and N 3200 (by Bayer), Tolonate® HDB and HDB-LV (by Rhodia) and Duranate® 24A-100 (by Asahi Kasei); HDI-isocyanurates, for example, as Desmodur® N 3300, N 3600 and N 3790 BA (all by Bayer), Tolonate® HDT, HDT-LV and HDT-LV2 (by Rhodia), Duranate® TPA-100 and THA-100 (by Asahi Kasei) and Coronate® HX (by Nippon Polyurethane); HDI-uretdiones, for example as Desmodur® N 3400 (by Bayer); HDI-iminooxadiazinediones, for example, as Desmodur® XP 2410 (by Bayer); HDI-allophanates, for example as Desmodur® VP LS 2102 (by Bayer); IPDI-isocyanurates, for example, in solution as Desmodur® Z 4470 (by Bayer) or in solid form as Vestanat® T1890/100 (by Degussa); TDI oligomers, for example, as Desmodur® IL (by Bayer); as well as mixed isocyanurates based on TDI/HDI, for example, as Desmodur® HL (by Bayer). In addition, the following can be suitable: forms of MDI (so-called "modified MDI") that are liquid at room temperature and that represent mixtures of MDI with MDI derivatives, such as, for example, MDI carbodiimides or MDI uretonimines or MDI urethanes, known, for example, under trade names such as Desmodur® CD, Desmodur® PF, Desmodur® PC (all by Bayer), as well as mixtures that contain MDI and MDI homologs (polymeric MDI or PMDI), available under trade names such as Desmodur® VL, Desmodur® VL50, Desmodur® VL R10, Desmodur® VL R20 and Desmodur® VKS 20F (all by Bayer), Isonate® M 309, Voranate® M 229 and Voranate® M 580 (all by Dow) or Lupranat® M 10 R (by BASF).

The above-mentioned oligomeric polyisocyanates PI can represent mixtures of substances with different degrees of oligomerization and/or chemical structures. They can have a mean NCO functionality of 2.1 to 4.0 and contain, for example, isocyanurate, iminooxadiazinedione, uretdione, urethane, biuret, allophanate, carbodiimide, uretonimine or oxadiazinetrione groups. These oligomers can have a low content of monomeric diisocyanates.

As polyisocyanate PI, the following can be used: forms of MDI that are liquid at room temperature, as well as the oligomers of HDI, IPDI and TDI, and, for example, the isocyanurates.

In an exemplary embodiment, a polyurethane polymer PUP that has isocyanate groups can be suitable as polyisocyanate P.

A suitable polyurethane polymer PUP that has isocyanate groups can be available by the reaction of at least one polyol with at least one polyisocyanate.

As polyols for the production of a polyurethane polymer PUP, for example, the following commercially available polyols or mixtures thereof can be used:

Polyoxyalkylene polyols, also called polyether polyols or oligoetherols, which are polymerization productions of ethylene oxide, 1,2-propylene oxide, 1,2- or 2,3-butylene oxide, oxetane, tetrahydrofuran or mixtures thereof, optionally polymerized using a starter molecule with two or more active hydrogen atoms, such as, for example, water, ammonia, or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, as well as mixtures of the above-mentioned compounds. Both polyoxyalkylene polyols, which have a low degree of unsaturation (measured according to ASTM D-2849-69 and indicated in milliequivalents of unsaturation per gram of polyol (mEq/g)), produced, for example, using so-called double metal cyanide complex catalysts (DMC Catalysts), and polyoxyalkylene polyols with a higher degree of unsaturation, produced, for example, using anionic catalysts, such as NaOH, KOH, CsOH or alkali alcoholates, can be used.

Polyoxyalkylene diols or polyoxyalkylene triols, for example, polyoxyethylene and polyoxypropylene di- and triols, can be suitable.

Polyoxyalkylene diols and -triols with a degree of unsaturation that is lower than 0.02 mEq/g and with a molecular weight in the range of 1,000-30,000 g/mol, as well as polyoxypropylene diols and -triols with a molecular weight of 400-8,000 g/mol, can be suitable.

So-called ethylene-oxide-terminated ("EO-endcapped," ethylene oxide-endcapped) polyoxypropylene polyols can be used. The latter are special polyoxypropylene polyoxyethylene polyols, which can be obtained, for example, in that pure polyoxypropylene polyols, for example, polyoxypropylene diols and -triols, are further alkoxylated after polypropoxylation reaction with ethylene oxide is completed and as a result have primary hydroxyl groups.

Styrene-acrylonitrile- or acrylonitrile-methylmethacrylate-plugged polyether polyols.

Polyester polyols, also called oligoesterols, produced according to known methods, for example, the polycondensation of hydroxycarboxylic acids or the polycondensation of aliphatic and/or aromatic polycarboxylic acids with divalent or multivalent alcohols.

Polyester polyols can include, for example, those produced from divalent to trivalent, for example, divalent, alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimer diol), hydroxypivalic acid neopentyl glycol ester, glycerol, 1,1,1-trimethylolpropane or mixtures of the above-mentioned alcohols, with organic di- or tricarboxylic acids, for example, dicarboxylic acids, or their anhydrides or esters, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethylterephthalate, hexahydrophthalic acid, trimellitic acid and trimellitic acid anhydride, or mixtures of the above-mentioned acids, as well as polyester polyols that include lactones, such as, for example, s-caprolactone and starters such as the above-mentioned divalent or trivalent alcohols.

Exemplary polyester polyols include polyester diols. Exemplary compounds include:

Polycarbonate polyols, as they are available by reaction, for example, of the above-mentioned alcohols—used to create polyester polyols—with dialkylcarbonates, diarylcarbonates or phosgene.

Block copolymers that carry at least two hydroxyl groups, which have at least two different blocks with polyether, polyester and/or polycarboxylic structures of the above-described type, for example, polyether polyester polyols.

Polyacrylate and polymethacrylate polyols.

Polyhydroxy-functional fats and oils, for example natural fats and oils, for example, castor oil; or—so-called oleochemical—polyols obtained by chemical modification of natural fats and oils, for example the epoxy polyester or epoxy polyether obtained by epoxidation of unsaturated oils and subsequent ring opening with carboxylic acids or alcohols, or polyols obtained by hydroformylation and hydrogenation of unsaturated oils; or polyols obtained from natural fats and oils by degradation process such as alcoholysis or ozonolysis and subsequent chemical cross-linking, for example by re-esterification or dimerization, of the thus obtained degradation products or derivatives thereof. Suitable degradation products of natural fats and oils include, for example, fatty acids and fatty alcohols, as well as fatty acid esters, for example, the methyl esters (FAME), which can be derivatized, for example, by hydroformylation and hydrogenation to form hydroxy fatty acid esters.

Polyhydrocarbon polyols, also called oligohydrocarbonols, such as, for example, polyhydroxy-functional polyolefins, polyisobutylenes, polyisoprenes; polyhydroxy-functional ethylene-propylene, ethylene-butylene or ethylene-propylene-diene copolymers, as they are produced, for example, by the Kraton Polymers Company; polyhydroxy-functional polymers of dienes, for example, 1,3-butadiene, which can be produced, for example, also from anionic polymerization; polyhydroxy-functional copolymers that include dienes such as 1,3-butadiene or diene mixtures and vinyl monomers, such as styrene, acrylonitrile, vinyl chloride, vinylacetate, vinyl alcohol, isobutylene and isoprene, for example polyhydroxy-functional acrylonitrile/butadiene copolymers, as they can be produced, for example, from epoxides or amino alcohols and carboxyl-terminated acrylonitrile/butadiene copolymers (for example, commercially availabe under the name Hypro® (earlier, Hycar®) CTBN and CTBNX and ETBN of Nanoresins AG, Germany, or Emerald Performance Materials LLC); as well as hydrogenated polyhydroxy-functional polymers or copolymers of dienes.

These above-mentioned polyols can have a mean molecular weight of 250-30,000 g/mol, for example, 400-20,000 g/mol, and, for example, can have a mean OH functionality in the range of 1.6 to 3.

In connection with the oligomers or polymers in this document, "molecular weight" is always defined as the molecular weight $M_n$.

As polyols, polyether-, polyester-, polycarbonate- and polyacrylate polyols, for example, di- and triols, can be used. Polyether polyols, for example, polyoxypropylene- and polyoxypropylene polyoxyethylene polyols, as well as liquid polyester polyols and polyether polyester polyols, can be used.

In addition to these above-mentioned polyols, small amounts of low-molecular divalent or multivalent alcohols, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimer fatty alcohols, 1,1,1-trimethylolethane, 1,1,1-trimethylolpropane, glycerol, pentaerythritol, sugar alcohols, such as xylitol, sorbitol or mannitol, sugars such as saccharose, other polyhydric alcohols, low-molecular alkoxylating products of the above-mentioned divalent and multivalent alcohols, as well as mixtures of the above-mentioned alcohols can be simultaneously used in the production of the polyurethane polymer PUP. Small amounts of polyols with a mean OH functionality of more than 3, for example, sugar polyols, can also be simultaneously used.

As polyisocyanates for the production of a polyurethane polymer PUP, aliphatic, cycloaliphatic, or aromatic polyisocyanates, for example, diisocyanates, can be used, for example the monomeric diisocyanates, which were already mentioned as suitable polyisocyanates PI, as well as oligomers and polymers of these monomeric diisocyanates, as well as any mixtures of these isocyanates. Monomeric diisocyanates, for example, MDI, TDI, HDI and IPDI, can be used.

The production of a polyurethane polymer PUP can be carried out in a known way directly from the polyisocyanates and the polyols, or by adduction methods in steps, as they are also known as chain-lengthening reactions.

In an exemplary embodiment, the polyurethane polymer PUP can be produced by a reaction of at least one polyisocyanate and at least one polyol, whereby the isocyanate groups relative to the hydroxyl groups can be present in stoichiometric excess. For example, the ratio between isocyanate and hydroxyl groups can be 1.3 to 10, for example, 1.5 to 5.

The polyurethane polymer PUP can have a molecular weight of, for example, above 500 g/mol, for example, such as one between 1,000 and 30,000 g/mol.

In addition, the polyurethane polymer PUP can have a mean NCO functionality in the range of 1.8 to 3.

As polyisocyanate P, the following can be suitable: mixtures that contain a polyurethane polymer PUP and a polyisocyanate PI, for example, on the one hand, mixtures that contain an MDI-based polyurethane polymer PUP and monomeric and/or polymeric MDI, as well as, on the other hand, mixtures that contain an IPDI-based polyurethane polymer PUP and monomeric and/or oligomeric IPDI.

Upon contact of the aldimine A with the polyisocyanate P, the HX groups as well as optionally present other groups that are reactive to isocyanate groups can react with the isocyanate groups in an addition reaction, while the aldimino groups do not react with the isocyanate groups in the absence of water. As soon as the aldimino groups come into contact with moisture, for example, in the form of atmospheric humidity, they can formally begin to hydrolyze to form aldehyde groups and primary amino groups, whereupon the latter react with the isocyanate groups and in this case form urea groups. The reaction of the isocyanate groups with the hydrolyzing aldimino groups does not necessarily have to be carried out with free primary amino groups. Reactions with intermediate stages of the hydrolysis reaction are also possible. For example, it is conceivable that a hydrolyzing aldimino group in the form of a semiaminal can react directly with an isocyanate group. In addition, isocyanate groups can also react directly with moisture and in this case form urea groups. Depending on stoichiometry between isocyanate groups and the sum of the groups relative to isocyanate groups, the composition can cure as a result of these reactions, which can also be referred to as cross-linking, or comparatively low-molecular addition products are formed from aldimines A and polyisocyanates P, which can be used for related reactions.

For the case that in this reaction, a clear excess of HX groups is present relative to the isocyanate groups, for example, addition products AV1 of Formula (XVII) can be formed,

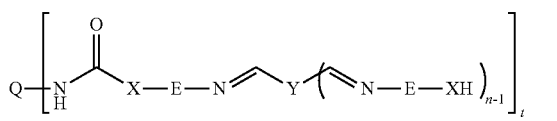

(XVII)

whereby

Q stands for the radical of a polyisocyanate P after removal of t isocyanate groups, t stands for 2 or 3, for example, for 2, and n, E, X and Y have the already mentioned meanings.

The addition products AV1 can be used in the same way as the aldimines A, for example, as curing agents for compositions having isocyanate groups.

For the case that in this reaction, a significant excess of isocyanate groups is present relative to the HX groups, for example, addition products AV2 of Formula (XVIII) can be formed with the exclusion of water,

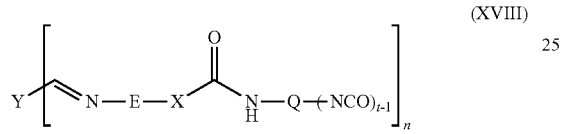

(XVIII)

whereby n, t, E, Q, X and Y have the already mentioned meanings.

The addition products AV2 can be substances that can be cured with moisture. They can be used, for example, as integral parts of compositions that can be cured with moisture.

The described composition can be a two-component composition.

In this document, a composition is referred to as "two-component" in which the integral parts of the composition can be present in two different components, which can be stored in compartments or barrels that are separated from one another and that in each case can have a long shelf life per se. For example, not until just shortly before or during the application of the composition are the two components mixed together, whereupon the mixed composition can be cured, whereby the curing can proceed or is completed, for example, only under the action of moisture under certain circumstances.

The described composition can be a curable two-component composition ZS, including a first component K1 that contains a) at least one aldimine A of Formula (I), as it was previously described, and b) at least one substance RS, which has at least two groups that are reactive to isocyanate groups, and/or water, and a second component K2 that contains c) at least one polyisocyanate P, as it was previously described.

As groups that are reactive to isocyanate groups in the substance RS, for example, hydroxyl, mercapto and primary or secondary amino groups can be suitable, whereby of the amino groups, the secondary groups can be used.

As the substance RS, which can have at least two groups that are reactive to isocyanate groups, for example, the following can be suitable:

Polyols with at least two hydroxyl groups, for example, polyols, which were previously described as suitable for the production of a polyurethane polymer PUP, as well as low-molecular alcohols, for example, the low-molecular alcohols that were previously described as suitable for the production of a polyurethane polymer PUP;

Polythiols with at least two mercapto groups, such as, for example, the liquid mercapto-terminated polymers that are known under the trade name Thiokol®, for example the types LP-3, LP-33, LP-980, LP-23, LP-55, LP-56, LP-12, LP-31, LP-32 and LP-2 (by Morton Thiokol; for example, available from SPI Supplies, USA, or from Toray Fine Chemicals, Japan), as well as polyesters from thiocarboxylic acids, for example, pentaerythritol tetramercaptoacetate, trimethylolpropane trimercaptoacetate, glycol dimercaptoacetate, pentaerythritol tetra-(3-mercaptopropionate), trimethylolpropanetri-(3-mercaptopropionate) and glycol di-(3-mercaptopropionate);

Thioalcohols with at least one hydroxyl group and at least one mercapto group, such as, for example, 2-mercaptoethanol, 1-mercapto-2-propanol, 3-mercapto-1-propanol, 3-mercapto-1,2-propanediol, 4-mercapto-1-butanol, or 6-mercapto-1-hexanol;

Polyamines with at least two secondary amino groups, such as, for example, N,N'-dibutylethylenediamine; N,N'-di-tert-butyl-ethylenediamine, N,N'-diethyl-1,6-hexanediamine, 1-(1-methylethyl-amino)-3-(1-methylethyl-aminomethyl)-3,5,5-trimethylcyclohexane (Jefflink® 754 by Huntsman), N4-cyclohexyl-2-methyl-N2-(2-methylpropyl)-2,4-pentanediamine, N,N'-dialkyl-1,3-xylylenediamine, bis-(4-(N-alkylamino)-cyclohexyl)-methane, 4,4'-trimethylene-dipiperidine as well as N-alkylated polyetheramines, for example the Jeffamine® types SD-231, SD-401, SD-404 and SD-2001 (by Huntsman);

Amino alcohols with at least one hydroxyl group and at least one secondary group, such as, for example, 2-(methylamino)ethanol, 2-(ethylamino)ethanol, 2-(butylamino)ethanol, 2-(cyclohexylamino)ethanol, 3-pyrrolidinol, 3- or 4-hydroxy-piperidine, 2-piperidineethanol, 2-[2-(1-piperazyl)]ethanol, 2-[2-(1-piperazyl)ethoxy]ethanol, N-hydroxyethylaniline, diethanolamine, diisopropanolamine, 3-methylamino-1,2-propanediol;

Polyamines with at least two primary amino groups, for example, polyoxy alkylene-polyamines, which represent products from the amination of polyoxyalkylene-polyols and are available, for example, under the name Jeffamine® (by Huntsman), under the name polyetheramine (by BASF) or under the name PC Amine® (by Nitroil); exemplary polyoxyalkylenediamines include Jeffamine® D-230, Jeffamine® D-400, Jeffamine® D-2000, Jeffamine® D-4000, Jeffamine® XTJ-568, Jeffamine® XTJ-569, Jeffamine® XTJ-523, Jeffamine® XTJ-536, Jeffamine® XTJ-542, Jeffamine® XTJ-559, Jeffamine® T-403, Jeffamine® T-5000, polyetheramine D 230, polyetheramine D 400, polyetheramine D 2000, polyetheramine T403, polyetheramine T5000; PC Amine® DA 250, PC Amine® DA 400, PC Amine® DA 650, PC Amine® DA 2000, PC Amine® TA 403, and PC Amine® TA 5000.

As the substance RS, polyols can be used that have a mean molecular weight of 250 to 30,000 g/mol, for example, 400 to 20,000 g/mol, and a mean OH functionality of 1.6 to 3.0.

In an exemplary embodiment, the curing two-component composition ZS is a composition ZS1 that includes a first component K1' that contains
 a) at least one aldimine A of Formula (I),
 b) at least one polyol D and optionally water,
and a second component K2' that contains
 c) at least one polyisocyanate P.

As polyol D, the polyols that were previously described as suitable for the production of a polyurethane polymer PUP and that have a mean molecular weight of 250 to 30,000 g/mol, for example, 400 to 20,000 g/mol, and a mean OH functionality of 1.6 to 3.0 can be suitable.

As polyol D, polyols can be selected from polyether polyols, polyester polyols, polyether polyester polyols, polycarbonate polyols, polyacrylate polyols, polyhydrocarbon polyols, and polyhydroxy-functional fats and oils.

In the composition ZS1, the ratio between the number of groups that are reactive to the isocyanate groups, and the number of isocyanate groups can be 0.5 to 1.1, for example, 0.6 to 1.0, for example, 0.65 to 0.95, whereby the aldimino groups are counted among the groups that are reactive to isocyanate groups, and existing water is counted as not among the groups that are reactive to isocyanate groups.

In the composition ZS1, the ratio between the number of aldimino groups and the number of isocyanate groups can be 0.05 to 0.3. The ratio between the number of hydroxyl groups and the number of HX groups can have a value of 1 to 50, for example, 2 to 20.

In an exemplary embodiment, the curing two-component composition ZS can be a composition ZS2 that includes a first component K1" that contains
 a) at least one aldimine A of Formula (I),
 b) water and optionally one surfactant,
and a second component K2" that contains
 c) at least one polyisocyanate P, for example, a polyurethane polymer PUP.

The component K2" can be formulated in such a way that upon contact with atmospheric humidity, it also cures by itself to form a cured composition with good mechanical properties; i.e., it can then also usable by itself and thus represent a one-component moisture-curing composition, for example a one-component polyurethane adhesive or sealant, as they are widely commercially available. For example, such adhesives are offered under the trade names Sikaflex® and SikaTack® by Sika Schweiz AG.

The component K1" is used, for example, for accelerating the curing of the component K2", optionally also for influencing the application properties and/or the mechanical properties. The component K1" can be present as emulsion.

In the composition ZS2, the ratio of the groups that are reactive to isocyanate groups and the number of isocyanate groups can be 0.1 to 0.7, for example, 0.1 to 0.5, whereby the aldimino groups are counted among the groups that are reactive to isocyanate groups and existing water is counted as not among the groups that are reactive to isocyanate groups.

In the composition ZS2, the water relative to the isocyanate groups can be present in an approximately stoichiometric or, for example, clearly hyperstoichiometric amount.

The curing two-component composition ZS optionally contains other integral parts, for example, adjuvants and additives capable of use in polyurethane compositions, for example the following:

Softeners, for example, carboxylic acid esters, such as phthalates, for example, dioctyl phthalate, diisononyl phthalate, and diisodecyl phthalate, adipates, for example, dioctyl adipate, azelates and sebacates, organic phosphoric and sulfonic acid esters and polybutenes;

Non-reactive thermoplastic polymers, such as, for example, homo- or copolymers of unsaturated monomers, for example, from the group that comprises ethylene, propylene, butylene, isobutylene, isoprene, vinyl acetate and alkyl(meth)acrylates, for example, polyethylene (PE), polypropylene (PP), polyisobutylene, ethylene vinyl acetate copolymers (EVA) and atactic poly-α-olefins (APAO);

Solvents;

Inorganic and organic fillers, for example, ground or precipitated calcium carbonate, which optionally are coated with fatty acids, for example, stearates, barite ($BaSO_4$, also called heavy spar), quartz flour, calcinated kaolins, aluminum oxides, aluminum hydroxides, silicic acids, for example, highly dispersed silicic acids from pyrolysis processes, carbon black, for example, industrially-produced carbon black (referred to as "carbon black," below), PVC powder and hollow spheres;

Fibers, for example made of polyethylene;

Pigments, for example titanium dioxide or iron oxides;

Catalysts, which accelerate the hydrolysis of aldimines, for example, acids, for example organic carboxylic acids such as benzoic acid, salicylic acid, and 2-nitrobenzoic acid, organic carboxylic acid anhydrides such as phthalic acid anhydride, hexahydrophthalic acid anhydride, and hexahydromethylphthalic acid anhydride, silyl esters from organic carboxylic acids, organic sulfonic acids such as methanesulfonic acid, p-toluenesulfonic acid, and 4-dodecylbenzenesulfonic acid, sulfonic acid esters, other organic or inorganic acids, or mixtures of the above-mentioned acids and acid esters;

Catalysts that accelerate the reaction of isocyanate groups, for example organotin compounds such as dibutyltin diacetate, dibutyltin dilaurate, dibutyltin dichloride, dibutyltin diacetylacetonate and dioctyltin dilaurate, bismuth compounds such as bismuth trioctoate and bismuth tris(neodecanoate), and compounds that contain tertiary amino groups, such as 2,2'-dimorpholinodiethylether and 1,4-diazabicyclo[2.2.2]octane;

Rheology modifiers such as, for example, thickeners or thixotropic agents, for example, urea compounds, polyamide waxes, bentonites or pyrogenic silicic acids;

Blocked amines, for example, in the form of ketimines, oxazolidines, enamines or other aldimines;

Desiccants, such as, for example, molecular sieves, calcium oxide, highly reactive isocyanates such as p-tosylisocyanate, orthoformic acid esters, alkoxysilanes such as tetraethoxysilane;

Organoalkoxysilanes, also called "silanes" below, such as, for example, epoxysilanes, (meth)acrylsilanes, isocyanatosilanes, vinyl silanes, carbamatosilanes, alkylsilanes, S-(alkylcarbonyl)-mercaptosilanes and aldiminosilanes, as well as oligomeric forms of these silanes;

Stabilizers to protect against heat, light and UV radiation;

Flame-retardant substances;

Surfactants such as, for example, wetting agents, flow enhancers, ventilating agents, or foam inhibitors;

Biocides such as, for example, algicides, fungicides, or substances that inhibit fungal growth.

When using such additional integral components, for example, it can be advantageous to ensure that the latter do not greatly impair the shelf life of the respective components K1 or K2. If such additives are present as integral parts of the component K2, for example, it can be ensured that during storage, they do not trigger the cross-linking of the isocyanate groups to a significant extent. In an exemplary embodiment, additives that are used in such a way do not contain any water or at most only traces of water. It can be useful, for example, to dry certain additives chemically or physically before mixing into the component K2.

In the case of the component K1, in addition still other adjuvants and additives can be used in addition to the latter, and said adjuvants and additives together with free isocyanate groups can have no—or only a brief—shelf life. For example, in the component K1, small amounts of polyamines can be present, as they were previously described as compounds C2, to obtain directly a structurally viscous, less strongly-flowing or sliding material with the mixing of the two components K1 and K2. In addition, catalysts can be present, such as, for example:

Compounds of zinc, manganese, iron, chromium, cobalt, copper, nickel, molybdenum, lead, cadmium, mercury, antimony, vanadium, titanium, zirconium or potassium, such as zinc(II) acetate, zinc(II) 2-ethylhexanoate, zinc(II) laurate, zinc(II) oleate, zinc(II) naphthenate, zinc(II) acetylacetonate, zinc(II) salicylate, manganese(II) 2-ethylhexanoate, iron(III) 2-ethylhexanoate, iron(III) acetylacetonate, chromium(III) 2-ethylhexanoate, cobalt(II) naphthenate, cobalt(II) 2-ethylhexanoate, copper(II) 2-ethylhexanoate, nickel(II) naphthenate, phenylmercuric neodecanoate, lead(II) acetate, lead(II) 2-ethylhexanoate, lead(II) neodecanoate, lead(II) acetylacetonate, aluminum lactate, aluminum oleate, aluminum(III) acetylacetonate, diisopropoxytitanium-bis-(ethylacetoacetate), dibutoxytitanium-bis-(ethylacetoacetate), dibutoxytitanium-bis-(acetylacetonate), potassium acetate, potassium octoate; tertiary amines, such as triethylamine, tributylamine, N-ethyl-diisopropylamine, N,N,N',N'-tetramethylethylenediamine, pentamethyl diethylene triamine and higher homologs thereof, N,N,N',N'-tetramethyl-propylenediamine, pentamethyl dipropylene triamine and higher homologs thereof, N,N,N',N'-tetramethyl-1,3-butanediamine, N,N,N',N'-tetramethyl-1,6-hexanediamine, bis-(dimethylamino)-methane, N,N-dimethylbenzylamine, N,N-dimethylcyclohexylamine, N-methyl-dicyclohexylamine, N,N-dimethyl-hexadecylamine, bis-(N,N-diethylaminoethyl)-adipate, N,N-dimethyl-2-phenylethylamine, tris-(3-dimethylaminopropyl)-amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N-methylmorpholine, N-ethylmorpholine, N-cocomorpholine, N,N'-dimethylpiperazine, N-methyl-N'-dimethylaminoethylpiperazine, bis-(dimethylaminoethyl)-piperazine, 1,3,5-tris-(dimethylaminopropyl)-hexahydrotriazine, bis-(2-dimethylaminoethyl)-ether; nitrogen-aromatic compounds such as 4-dimethylamino-pyridine, N-methylimidazole, N-vinylimidazole or 1,2-dimethylimidazole; amidines and guanidines such as 1,1,3,3-tetramethylguanidine; tertiary amines that contain active hydrogen atoms, such as triethanolamine, triisopropanolamine, N-methyldiethanolamine, N,N-dimethylethanolamine, 3-(dimethylamino)-propyl-diisopropanolamine, bis-(3-(dimethylamino)-propyl)-isopropanolamine, bis-(3-dimethylaminopropyl)amine, 3-(dimethylamino)-propyl-urea, Mannich bases of phenols such as 2,4,6-tris-(dimethylaminomethyl)-phenol and 2,4,6-tris-(3-(dimethylamino)-propylaminomethyl)-phenol, imidazoles such as N-hydroxypropylimidazole or N-(3-aminopropyl)-imidazole, as well as alkoxylating and polyalkoxylating products of these compounds, for example dimethylaminoethoxyethanol; organic ammonium compounds such as benzyltrimethylammonium hydroxide or alkoxylated tertiary amines; so-called "delayed-action" catalysts, which depict modifications of known metal or amine catalysts, such as reaction products from tertiary amines and carboxylic acids or phenols, for example from 1,4-diazabicyclo[2.2.2]octane or DBU and formic acid or acetic acid; as well as combinations of the above-mentioned compounds, for example, metal compounds and tertiary amines.

The composition ZS can contain at least one catalyst in the form of an organometallic compound and/or a tertiary amine and/or an acid, for example, an organic carboxylic acid or sulfonic acid.

In addition, the composition ZS can contain at least one filler.

The production of the two components K1 and K2 can be carried out separately from one another and, at least for the component K2, with exclusion of moisture. The two components K1 and K2 can have a long shelf life separate from one another; for example, they can each be stored for several months to a year or more before use in a suitable package or arrangement, such as, for example, a drum, a bag, a bucket, a cartridge, or a bottle, without changing in their respective properties to an extent that is relevant for their use. The component K1 can also have a long shelf life, for example, if it contains a certain amount of water, since hydrolysis of aldimines A proceeds to some extent in the absence of isocyanate groups.

For use of the described composition ZS, the two components K1 and K2 can be mixed together. In this case, the HX groups of the aldimine A, the optionally present groups of the substance RS that are reactive to isocyanate groups, as well as optionally present additional reactive groups that contain active hydrogen can begin to react directly with the isocyanate groups, whereby for example, urethane groups can be produced. The aldimino groups, for example, react only upon contact with moisture, by the aldimino groups, as already described previously, being hydrolyzed formally to form aldehyde groups and primary amino groups and the latter forming urea groups with isocyanate groups. The isocyanate groups that do not react with a group that is reactive to isocyanate groups can react directly with moisture and in this case form urea groups. As a result of these reactions, the composition ZS can cure; this process is also referred to as a cross-linking agent.

The mixing of the two components K1 and K2 can be carried out largely homogeneously or heterogeneously, whereby for mixing, for example, a static mixer or a dynamic mixer can be used, and the mixing can be carried out continuously or in batches. A mixed or partially mixed composition ZS can result from this.

In an exemplary embodiment, the mixing of the two components K1 and K2 can be carried out essentially homogeneously.

This can be achieved, for example, by the use of dynamic mixers. It is also possible, for example, to achieve an essentially homogeneous mixing by using static mixers with many mixing elements.

The term "homogeneously mixed," in the context of pasty compositions, for example, is not to be understood in absolute terms. The term means, for example, that mixing limits are no longer visible to the naked eye, but this is still entirely possible, for example, under a microscope. Based on experimental knowledge, it can be assumed that when using static mixers, for example of the Sulzer Quadro® type (available from the Sulzer Chemtech Company), the mixing of two pasty components is carried out essentially homogeneously with 18 or more static mixer elements.

The mixed composition ZS can then be applied to a substrate, optionally by means of a suitable application adjuvant.

It can be ensured that not too much time is lost between the mixing of the components and the application, since by too strong a preliminary reaction of the integral parts of the mixed composition before the application, the function of the cured composition can be disrupted, for example, by the adhesion to the substrate being built up only inadequately or in a delayed fashion. For example, the maximum time span, within which the mixed composition should be applied, is referred to as "open time."

With the mixing of the components K1 and K2, the mixed composition ZS can begin to cure via the already described reactions. The moisture that is used for the hydrolysis of the aldimino groups can penetrate in the form of atmospheric humidity into the mixed composition. The reaction of the aldimino groups can be carried out in a delayed manner, for example, from the outside to the inside, parallel to the penetration of the atmospheric humidity in the composition. The moisture can also be present partially or completely in the composition as early as at the beginning, for example, by being the integral part of the component K1. The aldimino groups can react somewhat more quickly with existing isocyanate groups, but nevertheless clearly slower than corresponding free amines. As a result of these reactions, the mixed composition can cross-link and ultimately cure to form a solid material.

The curing can be carried out in general without the formation of bubbles, even with higher curing speed. The curing speed can be influenced by the type and amount of one or more optionally present catalysts, by the temperature that prevails in the curing, and by the moisture that is available to the composition, for example, the atmospheric humidity.

The curing two-component composition ZS, as it was previously described, for example, can provide a series of advantages. The reaction of HX groups with isocyanate groups can be easily controllable and thus readily manageable open time of the composition-settable reaction, for example, when the HX groups are present in the form of the exemplary hydroxyl groups. Upon contact with moisture, the existing aldimino groups can then react very quickly with isocyanate groups. As a result, the composition can very quickly build up strength, for example, clearly faster than a comparable composition, which cures only with a polyol. In addition, by the hydrolysis of the aldimino groups, the direct reaction of isocyanate groups with moisture can be suppressed until the aldimino groups are for the most part reacted. At this point in time, the composition can already have a high strength, such that $CO_2$ released from the direct reaction of isocyanate groups with moisture is almost impervious to the formation of bubbles. In the hydrolysis of the aldimino groups of aldimines A, polyaldehydes ALD can be released with 2 to 4 aldehyde groups. The latter can have only relatively little moisture and remain largely in the cured composition, where they can cause only a little or no odor. The released polyaldehyde ALD in the cured composition can be very well tolerated and can have only a very slight softening effect on the composition. This can be advantageous, for example, when the composition is to have a high tensile strength and a high modulus of elasticity. The polyaldehydes ALD2, for example, the polyaldehydes ALD3, can be well tolerated in the cured composition. These exemplary advantageous properties of aldimines A can be presumably promoted by the special structure of the aldimines A. As a result, the polyaldehyde ALD can be released during hydrolysis has 2 to 4 aldehyde groups, its aldehyde equivalent weight can be relatively small, and for example, only a relatively small amount of aldehyde is released relative to the entire composition. In addition, the polyaldehydes ALD3, which are released from exemplary aldimines A3 of Formula (III a), can have functional groups that are capable of forming hydrogen bridge bonds. Potentially, the polyaldehydes ALD3 can be readily compatible and have very little softening effect in the cured composition. Compositions with aldimines A3 of Formula (III a) can show hardly any shrinkage and migration effects.

Aldimine A, in which the index n in Formula (I) stands for 3 or 4, for example, can show another exemplary advantageous effect. As a result of the aldimine A relative to the HX groups having a functionality of greater than 2, a high cross-linking and thus a quick build-up of strength can very quickly develop during curing. In the hydrolysis of the aldimino groups, the functionality of the aldimine curing agent—now the amine B—can then be reduced to 2, and a cured composition can be ultimately formed with the desired, readily settable final strength and elasticity. Thus, compositions with an especially high and quick early strength and good elasticity can be made available.

The previously described compositions can have exemplary advantages. For example, they can have a long enough open time to make possible good handling. The curing can then proceed very quickly, and without in this case a strong offensive odor occurring. In the cured state, the compositions can have high tensile strengths and moduli of elasticity and hardly any shrinkage and migration effects.

If in an exemplary embodiment the compositions contain only exemplary odorless aldimines A2 or A3 and otherwise no contents with a strong odor, no disruptive odor develops before, during and after the curing, which can be desirable for many applications, for example, in inside spaces.

The previously described compositions, for example, the composition ZS, can be used, for example, as an adhesive, a sealant, a filling compound, a coating, a floor covering, paint, varnish, or primer.

They can be suitable, for example, for applications in which a quick curing and a high strength are to be achieved in an open time that is not too short. These include, for example, applications as an adhesive, filling compound, coating, floor covering, paint and varnish.

Another exemplary aspect relates to a method for adhesive bonding a substrate S1 to a substrate S2, which comprises the steps:
i) application of a previously described composition to a substrate S1
ii) bonding of the applied composition to a substrate S2 within the open time of the composition;
or
i') application of a previously described composition to a substrate S1 and to a substrate S2;
ii') bonding of the applied composition together within the open time of the composition;
whereby the substrate S2 includes the same material or a different material such as the substrate S1.

Another exemplary aspect relates to a method for sealing. The method comprises the steps:
i") application of a previously described composition between a substrate S1 and a substrate S2, in such a way that the composition is in contact with the substrate S1 and the substrate S2;
whereby the substrate S2 includes the same material or a different material such as the substrate S1.

The sealant can be pressed into a so-called joint.

Another exemplary aspect relates to a method for coating a substrate S1. The method comprises the step:
i'") application of a previously described composition on a substrate S1 within the open time of the composition.

In this exemplary method, suitable substrates S1 and/or S2 can include, for example Glass, glass ceramic, concrete, mortar, brick, adobe, gypsum, and natural stone such as granite or marble;

Metals or alloys such as aluminum, steel, iron, nonferrous metals, galvanized metals;

Leather, textiles, paper, wood, resin-bonded wood products, resin-textile composite materials, and other so-called polymer composites;

Plastics such as polyvinyl chloride (hard and soft PVC), acrylonitrile-butadiene-styrene copolymers (ABS), SMC (sheet molding compounds), polycarbonate (PC), polyamide (PA), polyester, poly(methylmethacrylate) (PMMA), polyester, epoxide resins, polyurethanes (PUR), polyoxymethylene (POM), polyolefins (PO), polyethylene (PE) or polypropylene (PP), ethyllene/propylene copolymers (EPM) and ethylene/propylene/diene terpolymers (EPDM), whereby the plastics can be surface-treated by means of plasma, corona or flame;

Coated substrates such as powder-coated metals or alloys; as well as paints and varnishes.

The substrates can be pretreated, if necessary before the application of the composition. Such pretreatments can comprise, for example, physical and/or chemical cleaning methods, for example, grinding, sandblasting, brushing, or the like, or treatment with cleaners or solvents or the application of an adhesion promoter, an adhesion promoter solution or a primer.

The application of the mixed composition can be carried out in a broad temperature spectrum. For example, the composition can be applied at room temperature. The composition can also be applied at lower as well as at higher temperatures.

An article can be produced from these described methods for adhesive bonding, sealing or coating—or from the use of one of the described compositions as adhesive, sealant, filling compound, coating, floor covering, paint, varnish or primer.

This article can be, for example, a structure, for example, a structure above or below ground level, or an industrial item or a consumer item, for example, a window, a household appliance, or a means of transport, for example, a vehicle for water or land, for example, an automobile, a bus, a truck, a train or a boat, or an attached part of a means of transport, or an item of the furniture, textile or packaging industry.

EXAMPLES

1. Description of the Measuring Methods

Infrared spectra were measured on an FT-IR device 1600 by Perkin-Elmer (horizontal ATR measuring unit with ZnSe crystals). Liquid samples were applied in undiluted form as films, and solid samples were dissolved in $CH_2Cl_2$. The absorption bands are indicated in wave numbers ($cm^{-1}$) (measuring window: 4000-650 $cm^{-1}$).

$^1$H-NMR spectra were measured on spectrometer of the Bruker DPX-300 type at 300.13 MHz; the chemical shifts δ are indicated in ppm relative to tetramethylsilane (TMS); coupling constants J are indicated in Hz. No distinction was made among true and pseudo-coupling patterns.

The viscosity was measured on a thermostated cone-plate-viscosimeter Physica UM (cone diameter 20 mm, cone angle 1°, cone tip-plate-interval 0.05 mm, shear rate 10 to 1000 $s^{-1}$).

The amine content, i.e., the total content of aldimino groups and free amino groups in the produced compounds, was determined titrimetrically (with 0.1N of $HClO_4$ in glacial acetic acid, against crystal violet) and it is always indicated in mmol of N/g.

2. Production of Polyaldehydes 1,3-Bis-(2,2-dimethyl-3-oxopropyl)-imidazolidin-2-one In a round-bottom flask with a mounted reflux condenser, 21.5 g (0.25 mol) of 2-imidazolidinone, 41.7 g (0.50 mol) of 36% aqueous formaldehyde, and 37.2 g (0.52 mol) of isobutyraldehyde were introduced under nitrogen atmosphere while being stirred vigorously, and mixed with 5.0 g of concentrated hydrochloric acid, whereby the mixture boiled vigorously. After boiling had subsided, the mixture was heated to boiling in an oil bath (100° C.) for 3 hours. The colorless, clear reaction mixture was neutralized with 10N NaOH, extracted two times with ethyl acetate, the combined organic phases were washed with brine, dried on $MgSO_4$ and completely concentrated by evaporation in a rotary evaporator. The white crystal cake that was obtained was crushed and fractionated under high vacuum. The product distilled at a vapor temperature of 138° C. and a pressure of $4 \cdot 10^{-2}$ mbar. Yield: 45.9 g (72% of theory) of snow-white, odorless crystals with a melting point of 78-80° C. (uncorr.).

IR: 3433br, 2968, 2933, 2906, 2872, 2827, 2788, 2754, 2716 (CHO), 2685sh, 1757sh, 1719 (C=O aldehyde), 1682 (C=O urea), 1493, 1471, 1447, 1420, 1400, 1379, 1365, 1347, 1332, 1273, 1249, 1202, 1168, 1141, 1116, 1106, 1050, 1028, 1021sh, 992, 952, 909, 886, 870, 847sh, 775, 757, 671, 655.

$^1$H-NMR (CDCl$_3$, 300K): δ 9.56 (s, 2 H, CHO), 3.27 (2 x s, 2 x 4 H, NCH$_2$C(CH$_3$)$_2$ and NC(O)CH$_2$CH$_2$N), 1.09 (s, 12 H, NCH$_2$C(CH$_3$)$_2$).

N,N'-Bis(2,2-dimethyl-3-oxopropyl)-piperazine 166.8 g (2.00 mol) of 36% aqueous formaldehyde and 150.4 g (2.08 mol) of isobutyraldehyde were introduced into a round-bottom flask under nitrogen atmosphere. While being stirred vigorously and while being cooled with ice, 86.1 g (1.00 mol) of piperazine was slowly added in drops from an instillation funnel, whereby it was ensured that the temperature of the reaction mixture did not exceed 20° C. After the addition was completed, it was allowed to stir for one hour at room temperature. The viscous suspension that was produced was stirred under reflux in an oil bath at 120° C. for 18 hours. The clear, dark-orange reaction mixture was cooled to room temperature, whereby it crystallized completely. The solid mass was crushed with a pestle, suspended in water, and sucked off. The crude product was recrystallized from ethyl acetate. Yield (3 fractions): 161.1 g (63% of theory) of pale yellow, odorless crystal needles with an amine content of 7.78 mmol of N/g.

IR: 2964, 2938, 2871, 2795, 2752, 2688 (CHO), 1719 (C=O), 1463, 1400, 1374, 1360, 1341, 1323, 1283, 1152, 1123, 1054, 1017, 1005, 917, 869, 830, 775, 703.

$^1$H-NMR (CDCl$_3$, 300 K): δ 9.52 (s, 2H, CHO), 2.44 (s, 4H, NCH$_2$C(CH$_3$)$_2$), 2.39 (s, 8H, NCH$_2$CH$_2$$^{cycl.}$), 1.04 (s, 12H, CH$_2$C(CH$_3$)$_2$).

N,N,N',N'-Tetrakis-(2,2-dimethyl-3-oxopropyl)-urea

In a round-bottom flask with a mounted reflux condenser, 20.0 g (0.33 mol) of urea, 111.1 g (1.33 mol) of 36% aqueous formaldehyde, and 97.3 g (1.35 mol) of isobutyraldehyde were introduced under nitrogen atmosphere and, while being stirred vigorously, mixed with 5.0 g of concentrated hydrochloric acid, whereby the mixture heated considerably. After 10 minutes, the mixture was heated to boiling in an oil bath (120° C.) for 18 hours. The white, cloudy reaction mixture was neutralized with 10N NaOH, extracted twice with dichloromethane, the combined organic phases were washed with brine, dried on $MgSO_4$, and completely concentrated by evaporation in a rotary evaporator. The viscous oil that was obtained was distilled using a thin-film evaporator. Yield: 33.1 g (25% of theory) of pale yellow, viscous, odorless oil.

IR: 3370br, 2962, 2931sh, 2912sh, 2870, 2709 (CHO), 1721 (C=O aldehyde), 1640 (C=O urea), 1490, 1472, 1450, 1397, 1380, 1364, 1310, 1280, 1264, 1232, 1218, 1194, 1140, 1110, 1088, 1058, 1040, 1029sh, 1005, 986, 976sh, 948, 912, 894, 868, 844, 813, 772, 754, 735, 704.

N,N'-Bis-(2,2-dimethyl-3-oxopropyl)-urea

In a round-bottom flask with a mounted reflux condenser, 5.0 g (0.08 mol) of urea, 13.9 g (0.17 mol) of 36% aqueous formaldehyde, and 12.6 g (0.17 mol) of isobutyraldehyde were introduced under nitrogen atmosphere, and, while being stirred vigorously, mixed with 1.0 g of concentrated hydrochloric acid, whereby the mixture heated and formed clumps. After 10 minutes, the mixture was heated to boiling in an oil bath (120° C.) for 8 hours. The white, cloudy reaction mixture was neutralized with 10N NaOH, extracted twice with dichloromethane, the combined organic phases were washed with brine, dried on $MgSO_4$, and completely concentrated by evaporation in a rotary evaporator. Yield: 18.2 g of crude N,N'-bis-(2,2-dimethyl-3-oxopropyl)-urea as a colorless and odorless, viscous honey, which according to GC/MS analysis, had additional urea-aldehydes in portions, for example, N,N-bis-(2,2-dimethyl-3-oxopropyl)-urea and N,N,N'-tris-(2,2-dimethyl-3-oxopropyl)-urea.

IR: 3330br, 3057, 2967, 2932, 2911, 2871, 2716 (CHO), 1720 (C=O aldehyde), 1637br (C=O urea), 1490, 1449, 1403, 1378, 1367, 1304, 1265, 1204, 1141, 1086sh, 1055, 1039, 1029sh, 1003, 982, 953, 913, 894, 868, 838, 802, 759, 733, 701.

3. Production of Aldimines

Example 1

Aldimine A-1

In a round-bottom flask and under nitrogen atmosphere, 10.00 g (75 mmol) of terephthalaldehyde in 15.30 g of 2-(2-aminoethoxy)-ethanol (DGA; Diglycolamine® agent, Huntsman; amine content 9.46 mmol of N/g) was suspended and heated while being stirred, whereby the aldehyde quickly dissolved. Then, the volatile integral parts were removed in a vacuum (10 mbar, 80° C.). Yield: 22.7 g of slightly cloudy, brown-orange-colored oil with an amine content of 6.19 mmol of N/g, which, during cooling to room temperature, crystallized completely within a few hours. Melting point: 47-49° C. (uncorr.).

IR: 3370br (OH), 2910sh, 2857, 1933br, 1697, 1639 (C=N), 1607, 1567, 1506, 1441, 1416, 1371sh, 1355, 1339, 1298, 1216, 1162sh, 1120, 1058br, 1017sh, 967, 890br, 830, 813sh.

Example 2

Aldimine A-2

In a round-bottom flask and under nitrogen atmosphere, 10.00 g (39 mmol) of 1,3-bis-(2,2-dimethyl-3-oxopropyl)-imidazolidin-2-one was suspended in 7.84 g of 2-(2-aminoethoxy)-ethanol (DGA; Diglycolamine® agent, Huntsman; amine content 9.46 mmol of N/g), the mixture was heated while being stirred, and the volatile integral parts were removed in a vacuum (first 10 mbar, and then $4 \cdot 10^{-2}$ mbar, 80° C.), whereby the aldehyde was completely dissolved after approximately 30 minutes. Yield: 16.48 g of clear, colorless honey with an amine content of 4.46 mmol of N/g and a viscosity of 10.3 Pa·s at 20° C.

IR: 3390br (OH), 2954, 2925, 2907, 2864, 2717, 1682sh (C=O), 1666 (C=N), 1493, 1444, 1425sh, 1391, 1362, 1335, 1275, 1253, 1204sh, 1162sh, 1123, 1060, 997sh, 928sh, 900sh, 892, 813, 786, 757, 677, 660.

$^1$H-NMR ($CDCl_3$, 300K): δ 7.63 (t, J = 1.3, 2 H, CH = N), 3.70 and 3.56 (2 x m, 2 x 8 H, $HOCH_2CH_2OCH_2CH_2N$), 3.38 (br s, 2 H, OH), 3.31 and 3.18 (2 x s, 2 x 4 H, $NCH_2C(CH_3)_2$ and $\overline{NC(O)CH_2CH_2N}$), 1.09 (s, 12 H, $NCH_2C(CH_3)_2$).

Example 3

Aldimine A-3

In a round-bottom flask and under nitrogen atmosphere, 10.00 g of 2-(2-aminoethoxy)-ethanol (DGA; Diglycolamine® agent, Huntsman; amine content 9.46 mmol of N/g) was introduced. Within 5 minutes, 12.46 g (49 mmol) of finely ground N,N'-bis(2,2-dimethyl-3-oxopropyl)-piperazine was added to this with a spatula at room temperature, and the suspension that was produced was stored for 30 minutes at room temperature. Then, the mixture was heated in an oil bath, and the volatile components were removed in a vacuum (10 mbar, 85° C.). Yield: 20.78 g of slightly cloudy, bright-orange-colored oil with an amine content of 9.30 mmol of N/g and a viscosity of 1.95 Pa·s at 20° C.

IR: 3358br (OH), 2929, 2922, 2904, 2861, 2842, 2804, 1664 (C=N), 1458, 1441sh, 1378, 1358, 1336, 1320, 1280, 1235br, 1150, 1122, 1061, 1015, 890, 831.

$^1$H-NMR ($CDCl_3$, 300 K): δ 7.61 (s, 2H, CH=N), 3.71 and 3.56 (2×m, 2×8 H, all $OCH_2$), 2.42 (s, 8H, $NCH_2^{cycl.}$), 2.40 (br s, 2H, OH), 2.33 (s, 4H, $NCH_2C(CH_3)_2$), 1.04 (s, 12H, $CH_2C(CH_3)_2$).

Example 4

Aldimine A-4

In a round-bottom flask and under nitrogen atmosphere, 10.00 g (25 mmol) of N,N,N',N'-tetrakis-(2,2-dimethyl-3-oxopropyl)-urea was introduced, and at room temperature, 10.66 g of 2-(2-aminoethoxy)-ethanol (DGA; Diglycolamine® agent, Huntsman; amine content 9.46 mmol of N/g) was stirred in. Then, the mixture was heated in an oil bath, and the volatile integral parts were removed in a vacuum (first 10 mbar/80° C., and then $4 \cdot 10^{-2}$ mbar/100° C.). Yield: 16.1 g of pale yellow honey with an amine content of 3.07 mmol of N/g and a viscosity of 13.5 Pa·s at 50° C.

IR: 3380br (OH), 2959, 2929, 2909, 2866, 1710, 1662sh (C=N), 1642, 1634, 1489, 1472, 1446, 1393, 1361, 1308, 1262, 1232, 1221sh, 1192, 1125, 1084sh, 1058, 1007, 991sh, 977sh, 945, 908, 845, 804, 752, 733, 704, 662.

Example 5

Aldimine A-5

In a round-bottom flask and under nitrogen atmosphere, 15.00 g (66 mmol) of crude N,N'-bis-(2,2-dimethyl-3-oxo-propyl)-urea was introduced, and at room temperature, 12.50 g of 2-(2-aminoethoxy)-ethanol (DGA; Diglycolamine® agent, Huntsman; amine content 9.46 mmol of N/g) was stirred in. Then, the mixture was heated in an oil bath, and the volatile integral parts were removed in a vacuum (first 10 mbar/80° C., and then $4 \cdot 10^{-2}$ mbar/100° C.). Yield: 25.9 g of slightly cloudy, pale yellow oil with an amine content of 4.86 mmol of N/g and a viscosity of 5.2 Pa·s at 20° C.

IR: 3350br (OH), 2948, 2924, 2910, 2862, 1661sh (C=N), 1642, 1490, 1451, 1378sh, 1365, 1352, 1303, 1274, 1203, 1122, 1058, 984, 955, 894, 839, 802, 760.

Comparison Example 6

Aldimine A-6

In a round-bottom flask and under nitrogen atmosphere, 28.06 g (0.099 mol) of 2,2-dimethyl-3-lauroyloxy-propanal was introduced. While being stirred vigorously, 10.00 g (0.095 mol) of 2-(2-aminoethoxy)-ethanol (DGA; Diglycolamine® agent, Huntsman; amine content 9.46 mmol of N/g) was added from an installation funnel. Then, the volatile integral parts were removed in a vacuum (10 mbar, 80° C.). Yield: 36.3 g of colorless, clear and odorless liquid that is thin fluid at room temperature with an amine content of 2.58 mmol of N/g.

4. Production of Two-Component Polyurethane Compositions

Examples 7 to 10, Comparison Examples 11 and 12

Filling Compounds

For each example, the respective integral parts of component K1 according to Table 1 were weighed in the indicated parts by weight without previous drying in a polypropylene beaker with a screw closure and mixed by means of a centrifugal mixer (SpeedMixer™ DAC 150, FlackTek Inc.; 2 min. at 3000 rpm) to form a homogeneous cream. The parts by weight of PMDI indicated in Table 1 were added to this as component K2 and mixed in homogeneously (30 seconds at 3000 rpm). The ratio between the isocyanate groups of the component K2 and the sum of the reactive groups (hydroxyl- and aldimine groups) of component K1 is always 1.1.

The castor oil that was used was by Fluka and had an OH number of 165 mg of KOH/g. As a dimer fatty acid diol, Sovermol® 908 by Cognis with an OH number of 200 mg of KOH/g was used. As a triol, Desmophen® 4011 T by Bayer with an OH number of 550 mg of KOH/g was used. As an acid catalyst, a solution of 5% by weight of salicylic acid in dioctyl adipate was used. As chalk, Omyacarb® 5-GU by Omya was used. The PMDI was Desmodur® VKS 20 F by Bayer with an NCO content of 30.0% by weight.

TABLE 1

Composition of Examples 7 to 11

| | Example | | | | |
|---|---|---|---|---|---|
| | 7 | 8 | 9 | 10 (Cf.) | 11 (Cf.) |
| Component K1: | | | | | |
| Castor Oil | 22.5 | 22.5 | 22.5 | 22.5 | 22.5 |
| Dimer Fatty Acid Diol | 17.5 | 17.5 | 17.5 | 17.5 | 17.5 |
| Triol | 4.75 | 4.75 | 4.75 | 4.75 | 4.75 |
| Aldimine | A-1 5.0 | A-2 5.0 | A-3 5.0 | A-6 5.0 | — |
| Tripropylene Glycol | — | — | — | — | 5.0 |
| Acid Catalyst | 0.25 | 0.25 | 0.25 | 0.25 | 0.25 |
| Chalk | 50.0 | 50.0 | 50.0 | 50.0 | 50.0 |
| Component K2: | | | | | |
| PMDI | 36.5 | 33.9 | 34.0 | 31.0 | 35.0 |

The thus obtained mixed compositions (filling compounds) were tested for open time, curing speed, and mechanical properties after curing. The open time of the filling compound was referred to as "good" when the latter could be poured easily up to a maximum of 3 minutes after the mixing of the two components K1 and K2 at room temperature and thus could be processed as desired, i.e., exhibited no viscosity increase that would prevent or preclude processing. References to curing speed were obtained, on the one hand, by measuring the time until freedom from adhesion ("tack-free time")—referred to in the table as "freedom from adhesion." To this end, the filling compound was applied in a layer thickness of approximately 2 mm on a piece of cardboard directly after the mixing of the two components K1 and K2, and under normal climatic conditions (23±1° C., 50±5% relative atmospheric humidity), the time was determined that it took until—with a slight tilting of the surface of the filling compound by means of a pipette that includes LDPE—for the first time no residues remain on the pipette. On the other hand, the further course of the curing (and thus indirectly the strength build-up) was tracked by periodic measuring of the Shore D hardness according to DIN EN 53505. In this case, storage of 4 hours at 105° C. of the test piece cured for 7 days under normal climatic conditions was referred to as "post-cured." To test the mechanical properties, the filling compound was poured as a film with a layer thickness of approximately 2 mm into a flat PTFE mold; the film cured for 7 days under normal climatic conditions, and it was tested for tensile strength, elongation at break and modulus of elasticity (E-Modulus) at 0.5-1.0% expansion (drawing speed: 10 mm/minute) according to DIN EN 53504. In addition, the bubble formation (based on the amounts of bubbles, which occurred during the curing of the film) as well as the odor were evaluated qualitatively.

The results of these tests are cited in Table 2.

TABLE 2

Properties of Examples 7 to 11

| | Example | | | | |
|---|---|---|---|---|---|
| | 7 | 8 | 9 | 10 (Cf.) | 11 (Cf.) |
| Open Time | Good | Good | Good | Good | Good |
| Freedom from Adhesion [Minutes] | 15 | 37 | 13 | 52 | 108 |
| Shore D After 1 Day | 92 | 83 | 91 | 62 | 71 |
| Shore D After 3 Days | 96 | 92 | 96 | 84 | 84 |
| Shore D After 7 Days | 96 | 95 | 97 | 88 | 86 |
| Post-Cured Shore D | 98 | 96 | 98 | 92 | 94 |
| Tensile Strength [MPa] | 29.7 | 22.7 | 32.0 | 10.6 | 9.6 |
| Elongation at Break [%] | 3 | 5 | 3 | 50 | 30 |
| E-Modulus [MPa] | 1640 | 1050 | 1830 | 210 | 250 |
| Bubble Formation | None | None | None | None | Many |
| Odor | Slight | None | None | None | None |

It can be seen from Table 2 that the filling compounds of Examples 7 to 9 have a sufficiently long open time for processing and a very quick curing without forming bubbles. After a few days, they already reach their final hardness under normal climatic conditions. Post-curing is not necessary. They have very high tensile strengths and E-moduli. The filling compounds of Comparison Example 10, which contains the same amount of aldimine derived from a long-chain monoaldehyde, cures significantly slower and has a lower tensile strength and a lower E-modulus. The filling compounds of Comparison Example 11, which contains the same amount of a glycol instead of an aldimine, also cures more slowly, has a lower tensile strength and a lower E-modulus, and shows significant bubble formation during curing. During curing, the filling compound of Example 7 has a slight odor, while those of Examples 8 to 11 are odorless.

Examples 12 to 15 and Comparison Example 16

Adhesives

For each example, the respective integral parts of the component K1 according to Table 3 were weighed in the indicated parts by weight without previous drying in a polypropylene beaker with a screw closure and mixed by means of a centrifugal mixer (SpeedMixer™ DAC 150, FlackTek Inc.; 2 minutes at 3000 rpm) to form a homogeneous cream. The parts by weight of component K2, indicated in Table 3, which was produced as described below, were added to this and mixed in (30 seconds at 3000 rpm). The ratio between the isocyanate groups of component K2 and the sum of the reactive groups (hydroxyl and aldimine groups) of component K1 is always 1.1.

The component K2 was produced as follows:
30 parts by weight of PMDI (Desmodur® VKS 20 F, Bayer; NCO content=30.0% by weight), 10 parts by weight of modified MDI (Desmodur® CD, Bayer; NCO content=29.5% by weight), and 60 parts by weight of polyurethane polymer P-1 were mixed homogeneously in a mixer with exclusion of moisture.

The polyurethane polymer P-1 was produced as follows:
1300 g of polyoxypropylene-diol (Acclaim® 4200 N, Bayer; OH number 28.5 mg of KOH/g), 2600 g of polyoxypropylene polyoxyethylene triol (Caradol® MD34-02, Shell; OH number 35.0 mg of KOH/g), 600 g of 4,4'-methylene diphenyl diisocyanate (4,4'-MDI; Desmodur® 44 MC L, Bayer), and 500 g of diisodecyl phthalate (DIDP; Palatinol® Z, BASF) were reacted according to a known method at 80° C. to form an NCO-terminated polyurethane polymer with a content of free isocyanate groups of 2.05% by weight.

The same as for Example 7 was used as castor oil, as chalk, and as acid catalyst. The polypropylene glycol Acclaim® 4200 by Bayer with an OH number of 28.5 mg of KOH/g was used as polyol. Purmol® 13 by Zeochem Europe (in activated form) was used as a molecular sieve. DABCO® 33-LV by Air Products was used as an amine catalyst.

TABLE 3

Composition of Examples 12 to 16

| | Example | | | | |
|---|---|---|---|---|---|
| | 12 | 13 | 14 | 15 | 16 (Cf.) |
| Component K1: | | | | | |
| Castor Oil | 9.0 | 9.0 | 9.0 | 9.0 | 9.0 |
| Polyol | 35.0 | 35.0 | 35.0 | 35.0 | 35.0 |
| Aldimine | A-2 | A-3 | A-4 | A-5 | A-6 |
| | 5.0 | 5.0 | 5.0 | 5.0 | 5.0 |
| Chalk | 48.0 | 48.0 | 48.0 | 48.0 | 48.0 |
| Molecular Sieve | 2.0 | 2.0 | 2.0 | 2.0 | 2.0 |
| Amine Catalyst | 0.1 | 0.1 | 0.1 | 0.1 | 0.1 |
| Acid Catalyst | 0.9 | 0.9 | 0.9 | 0.9 | 0.9 |
| Component K2: | 31.7 | 31.4 | 25.9 | 32.9 | 25.0 |

The thus obtained mixed compositions (adhesives) were essentially tested in the same way as described for Example 7. Instead of Shore D hardness, however, the Shore A hardness was measured; the tensile strength, the elongation at break, and the E-modulus were tested on films with a layer thickness of 3 mm and with a drawing speed of 200 mm/minute, and the E-modulus was measured at 0.5-5.0% expansion. The results of these tests are cited in Table 4.

TABLE 4

Properties of Examples 12 to 16

| | Example | | | | |
|---|---|---|---|---|---|
| | 12 | 13 | 14 | 15 | 16 (Cf.) |
| Open Time | Good | Good | Good | Good | Good |
| Freedom from Adhesion [Minutes] | 60 | 25 | 30 | 50 | 105 |
| Shore A After 8 Hours | 20 | 39 | 33 | 33 | 12 |
| Shore A After 1 Day | 54 | 57 | 52 | 54 | 45 |
| Shore A After 2 Days | 58 | 59 | 56 | 57 | 52 |
| Shore A After 3 Days | 61 | 62 | 59 | 60 | 56 |
| Shore A After 7 Days | 62 | 63 | 60 | 61 | 58 |
| Post-Cured Shore A | 64 | 60 | 60 | 60 | 62 |
| Tensile Strength [MPa] | 2.1 | 2.0 | 2.2 | 1.2 | 1.6 |
| Elongation at Break [%] | 100 | 115 | 100 | 95 | 75 |
| E-Modulus [MPa] | 3.6 | 2.2 | 4.3 | 2.0 | 3.7 |
| Bubble Formation | None | None | None | None | None |
| Odor | None | None | None | None | None |

It can be seen from Table 4 that the adhesives of Examples 12 to 15 have an open time that is long enough for processing, a quick and bubble-free curing, as well as a high tensile strength and a high E-modulus. The adhesives of Examples 13 and 14 have an especially high curing speed; with the adhesive of Example 13, this can possibly be attributed to the additional catalytic effect of the tertiary amino groups in the aldehyde part of the aldimine A-3, while with the adhesive of Example 14, the high OH functionality of the aldimine A-4 is possibly jointly responsible for the quick strength build-up.

Thus, it will be appreciated by those skilled in the art that the present invention can be embodied in other specific forms without departing from the spirit thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A composition suitable for use in an adhesive, sealant, filling compound, coating or floor covering, the composition comprising:
    a) at least one aldimine A of Formula (I),

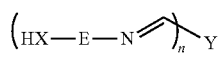
(I)

wherein n stands for 2 or 3 or 4,
E either represents a divalent hydrocarbon radical with 3 to 20 C atoms, or together with $R^{11}$ form a trivalent hydrocarbon radical with 3 to 20 C atoms, wherein E optionally contains heteroatoms in the form of ether-oxygen or tertiary amine-nitrogen,
Y represents an n-value organic radical with 6 to 30 C atoms, which optionally contains nitrogen and/or oxygen atoms in the form of tertiary amino groups, or ether, ester, carbonate, amide, urethane or urea groups,
X represents O or S or N—$R^{10}$ or N—$R^{11}$, wherein
    $R^{10}$ represents a monovalent hydrocarbon radical with 1 to 20 C atoms, which optionally contains at least one carboxylic acid ester, nitrile, nitro, phosphonic acid ester, sulfonic or sulfonic acid ester group, and
    $R^{11}$ together with E represents a trivalent hydrocarbon radical with 3 to 20 C atoms, which optionally contains heteroatoms in the form of ether-oxygen or tertiary amine-nitrogen; and
    b) at least one polyisocyanate P.

2. The composition according to claim 1, wherein the aldimine A has Formula (II)

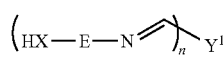
(II)

wherein $Y^1$ represents an n-value, substituted or unsubstituted aryl or heteroaryl radical, which has a ring size of 5 to 8 atoms.

3. The composition according to claim 1, wherein the aldimine A has Formula (III)

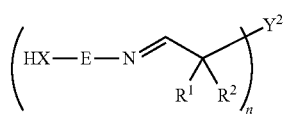
(III)

wherein
$R^1$ and $R^2$ either
independently of one another in each case represents a monovalent hydrocarbon radical with 1 to 12 C atoms, or
together represent a divalent hydrocarbon radical with 4 to 12 C atoms, which is part of an optionally substituted, carbocyclic ring with 5 to 8 C atoms;
$y^2$ represents an n-value organic radical with 1 to 24 C atoms, which optionally contains nitrogen and/or oxygen atoms in the form of tertiary amino groups, or ether, ester, carbonate, amide, urethane or urea groups.

4. The composition according to claim 3, wherein the aldimine A has Formula (III a)

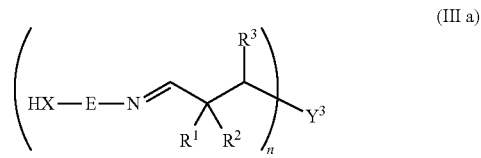
(III a)

wherein $R^3$ represents a hydrogen atom or an alkyl, cycloalkyl,
arylalkyl or alkoxycarbonyl radical with 1 to 12 C atoms;
$Y^3$ represents an n-value radical selected from the group consisting of

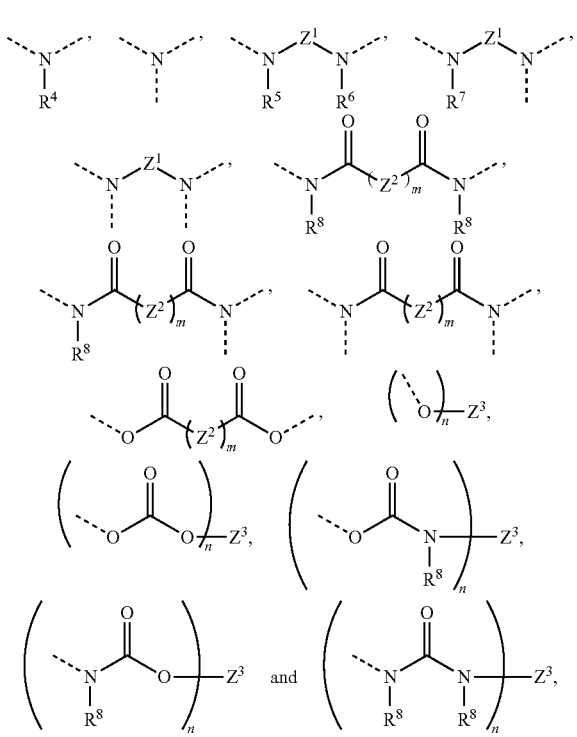

wherein
m represents 0 or 1;
$Z^1$ represents a carbonyl group or an alkylene radical with 2 to 15 C atoms, which optionally has at least one ether group;
$Z^2$ represents a divalent hydrocarbon radical with 1 to 15 C atoms, which optionally has at least one ether, carbonyl or carboxyl group;

Z³ represents an n-value hydrocarbon radical with 2 to 15 C atoms, which optionally has at least one ether or carbonyl group;

R⁴ represents an alkyl, cycloalkyl or arylalkyl radical with 1 to 20 C atoms;

R⁵ and R⁶ either
  independently of one another in each case represents an alkyl, cycloalkyl or arylalkyl radical with 1 to 12 C atoms,
  or, for the case that $Z^1$ represents a carbonyl group, independently of one another in each case represents a hydrogen atom or an alkyl, cycloalkyl or arylalkyl radical with 1 to 12 C atoms;
  or together represent an alkylene radical with 2 to 20 C atoms, which together with N—$Z^1$—N form a 5- to 12-membered ring and optionally has at least one ether group;

R⁷ either
  represents an alkyl, cycloalkyl or arylalkyl radical with 1 to 15 C atoms;
  or, for the case that $Z^1$ represents a carbonyl group, represents a hydrogen atom or an alkyl, cycloalkyl or arylalkyl radical with 1 to 15 C atoms;
  and R⁸ represents a hydrogen atom or an alkyl, cycloalkyl or arylalkyl radical with 1 to 8 C atoms.

5. The composition according to claim 4, wherein $Y_3$ represents the radical

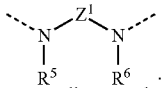

6. The composition according to claim 1, wherein the aldimine of Formula (I) is produced from a reaction of at least one amine B of Formula (IV) with at least one polyaldehyde ALD of Formula (V)

(IV)

(V)

wherein the amine B of Formula (IV) is selected from the group consisting of 5-amino-1-pentanol, 6-amino-1-hexanol or higher homologs thereof, 4-(2-aminoethyl)-2hydroxyethylbenzene, 3-aminomethyl-3,5,5-trimethyl-cyclohexanol, 2-(2-aminoethoxy)-ethanol, triethylene glycol-monoamine or higher homologs thereof, 3-(2-hydroxyethoxy)-propylamine, 3-(2-(2-hydroxyethoxy)-ethoxy)-propylamine, 3-(6-hydroxyhexyloxy)-propylamine, N-methyl-1,3-propanediamine, N-ethyl-1,3-propanediamine, N-butyl-1,3-propanediamine, N-(2-ethylhexyl)-1,3-propanediamine, N-dodecyl-1,3-propanediamine, N-cyclohexyl-1,3-propanediamine, N-coco alkyl-1,3-propanediamine, N-oleyl-1,3-propanediamine, N-soya alkyl-1,3-propanediamine, N-tallowalkyl-1,3-propanediamine and N-($C_{16-22}$-alkyl)-1,3-propanediamine.

7. The composition according to claim 1, wherein the composition is a two-component composition and comprises a component K1 that contains
  a) the at least one aldimine A of Formula (I), and
  b) at least one substance RS, which has at least two groups that are reactive to isocyanate groups, and/or water, and a component K2 that contains
  c) the at least one polyisocyanate P.

8. An addition product AV obtained from the composition according to claim 1, wherein the addition product is obtained by a reaction of the at least one aldimine A of Formula (I) with the at least one polyisocyanate P.

9. The addition product according to claim 8, wherein the addition product AV has Formula (XVII)

(XVII)

wherein Q represents the radical of a polyisocyanate P after removal of t isocyanate groups, and t represents 2 or 3.

10. The addition product according to claim 8, wherein the addition product AV has Formula (XVIII)

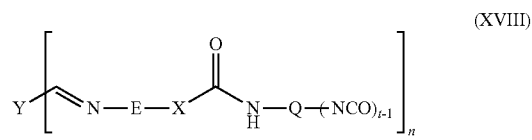

(XVIII)

wherein Q represents the radical of a polyisocyanate P after removal of t isocyanate groups, and t represents 2 or 3.

11. An aldimine, suitable for use in an adhesive, sealant, filling compound, coating or floor covering, of Formula (III)

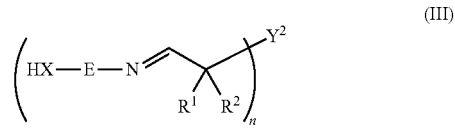

(III)

wherein

R¹ and R² either
  independently of one another in each case represents a monovalent hydrocarbon radical with 1 to 12 C atoms,
or
  together represent a divalent hydrocarbon radical with 4 to 12 C atoms, which is part of an optionally substituted, carbocyclic ring with 5 to 8 C atoms;

Y² represents an n-value organic radical with 1 to 24 C atoms, which optionally contains nitrogen and/or oxygen atoms in the form of tertiary amino groups, or ether, ester, carbonate, amide, urethane or urea groups;

E either represents a divalent hydrocarbon radical with 3 to 20 C atoms, or together with R¹¹ represents a trivalent hydrocarbon radical with 3 to 20 C atoms, wherein E optionally contains heteroatoms in the form of ether-oxygen or tertiary amine-nitrogen, X represents O or S or N—R¹⁰ or N—R¹¹, wherein R¹⁰ represents a monovalent hydrocarbon radical with 1 to 20 C atoms, which optionally contains at least one carboxylic acid ester, nitrile, nitro, phosphonic acid ester, sulfonic or sulfonic acid ester group, and R¹¹ together with E represents a trivalent hydrocarbon radical with 3 to 20 C atoms, which optionally contains heteroatoms in the form of ether-oxygen or tertiary amine-nitrogen;

and n represents 2 or 3 or 4.

12. The aldimine according to claim 11, wherein the aldimine has Formula (III a)

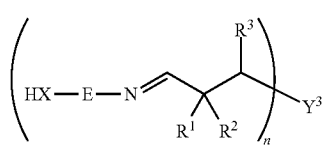

wherein
R³ represents a hydrogen atom or an alkyl, cycloalkyl, arylalkyl or alkoxycarbonyl radical with 1 to 12 C atoms;
Y³ represents an n-value radical that is selected from the group consisting of

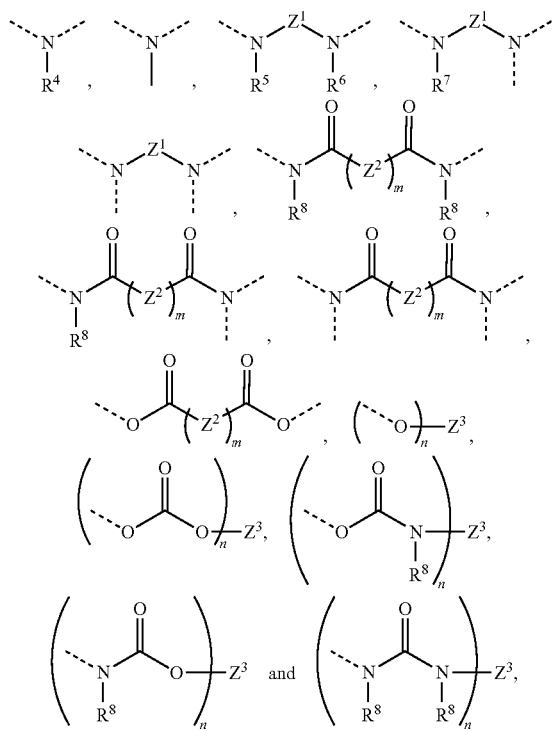

wherein
m represents 0 or 1;
Z¹ either represents a carbonyl group or an alkylene radical with 2 to 15 C atoms, which optionally contains at least one ether group;
Z² represents a divalent hydrocarbon radical with 1 to 15 C atoms, which optionally contains at least one ether, carbonyl or carboxyl group;
Z³ represents an n-value hydrocarbon radical with 2 to 15 C atoms, which optionally contains at least one ether or carbonyl group;
R⁴ represents an alkyl, cycloalkyl or arylalkyl radical with 1 to 20 C atoms;
R⁵ and R⁶ either
  independently of one another in each case represents an alkyl, cycloalkyl or arylalkyl radical with 1 to 12 C atoms,
  or, for the case that Z¹ represents a carbonyl group, independently of one another in each case represents a hydrogen atom or an alkyl, cycloalkyl or arylalkyl radical with 1 to 12 C atoms;
  or together represent an alkylene radical with 2 to 20 C atoms, which together with N—Z¹—N forms a 5- to 12-membered ring and optionally contains at least one ether group;
R⁷ either
  represents an alkyl, cycloalkyl or arylalkyl radical with 1 to 15 C atoms;
  or, for the case that Z¹ represents a carbonyl group, represents a hydrogen atom or an alkyl, cycloalkyl or arylalkyl radical with 1 to 15 C atoms;
and R⁸ represents a hydrogen atom or an alkyl, cycloalkyl or arylalkyl radical with 1 to 8 C atoms.

13. A method for adhesive bonding a substrate S1 to a substrate S2, comprising:
i) applying a composition to a substrate S1; and
ii) bonding the applied composition to a substrate S2 within an open time of the composition;
or
i') applying a composition to a substrate S1 and to a substrate S2; and
ii') bonding the applied composition together within an open time of the composition;
wherein the substrate S2 is formed from the same or different material as the substrate S1, and
wherein the composition comprises:
a) at least one aldimine A of Formula (I),

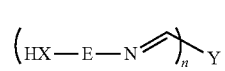

wherein n stands for 2 or 3 or 4,
E either represents a divalent hydrocarbon radical with 3 to 20 C atoms, or together with R¹¹ form a trivalent hydrocarbon radical with 3 to 20 C atoms, wherein E optionally contains heteroatoms in the form of ether-oxygen or tertiary amine-nitrogen,
Y represents an n-value organic radical with 6 to 30 C atoms, which optionally contains nitrogen and/or oxygen atoms in the form of tertiary amino groups, or ether, ester, carbonate, amide, urethane or urea groups,
X represents O or S or N—R¹⁰ or N—R¹¹, wherein
  R¹⁰ represents a monovalent hydrocarbon radical with 1 to 20 C atoms, which optionally contains at least one carboxylic acid ester, nitrile, nitro, phosphonic acid ester, sulfonic or sulfonic acid ester group, and
  R¹¹ together with E represents a trivalent hydrocarbon radical with 3 to 20 C atoms, which optionally contains heteroatoms in the form of ether-oxygen or tertiary amine-nitrogen; and
b) at least one polyisocyanate P.

14. A cured composition obtained from the composition according to claim 1 and moisture.

15. The cured composition according to claim 14, wherein the cured composition is suitable for use as an adhesive, sealant, filling compound, coating, floor covering, paint, varnish or primer.

16. The composition according to claim 2, wherein Y¹ represents an n-value, substituted or unsubstituted aryl or heteroaryl radical, which has a ring size of 6 atoms.

17. The composition according to claim 3, wherein R¹ and R² together represent a divalent hydrocarbon radical with 4 to 12 C atoms, which is part of an optionally substituted, carbocyclic ring with 6 C atoms.

18. The addition product according to claim 9, wherein t represents 2.

19. The addition product according to claim 10, wherein t represents 2.

20. The aldimine according to claim 11, wherein $R^1$ and $R^2$ together represent a divalent hydrocarbon radical with 4 to 12 C atoms, which is part of an optionally substituted, carbocyclic ring with 6 C atoms.

21. The composition according to claim 1, wherein in Formula (I), X represents O.

22. The aldimine according to claim 11, wherein in Formula (III), X represents O.

23. The method according to claim 13, wherein in Formula (I), X represents O.

* * * * *